US012109149B2

(12) United States Patent
Sacks et al.

(10) Patent No.: US 12,109,149 B2
(45) Date of Patent: Oct. 8, 2024

(54) AVOIDING BLOOD VESSELS DURING DIRECT SELECTIVE LASER TRABECULOPLASTY

(71) Applicant: BELKIN LASER LTD., Yavne (IL)

(72) Inventors: Zachary Sacks, Modiin (IL); Daria Lemann-Blumenthal, Bitzaron (IL); Daniel Elkayam, Rehovot (IL); Masha Dobkin-Bekman, Rishon Lezyon (IL)

(73) Assignee: BELKIN VISION LTD., Yavne (IL)

( * ) Notice: Subject to any disclaimer, the term of this patent is extended or adjusted under 35 U.S.C. 154(b) by 702 days.

(21) Appl. No.: 17/136,052

(22) Filed: Dec. 29, 2020

(65) Prior Publication Data

US 2021/0113373 A1 Apr. 22, 2021

Related U.S. Application Data

(63) Continuation-in-part of application No. PCT/IB2019/055564, filed on Jul. 1, 2019.

(Continued)

(51) Int. Cl.
*A61F 9/008* (2006.01)
*A61B 90/00* (2016.01)
*A61F 9/007* (2006.01)

(52) U.S. Cl.
CPC .............. *A61F 9/008* (2013.01); *A61B 90/04* (2016.02); *A61F 9/0079* (2013.01);
(Continued)

(58) Field of Classification Search
CPC .... A61F 9/008; A61F 9/0079; A61F 9/00823; A61F 2009/00868; A61F 2009/00891;
(Continued)

(56) References Cited

U.S. PATENT DOCUMENTS 2,635,502 A 4/1953 Richards
3,594,072 A 7/1971 Feather
(Continued)

FOREIGN PATENT DOCUMENTS

AU 2015210430 A1 9/2015
AU 2015315113 B2 3/2016
(Continued)

OTHER PUBLICATIONS

International Application # PCT/IB2021/059821 Search Report dated Apr. 7, 2022.
SG Application # 11202010437T Office Action dated May 13, 2022.
U.S. Appl. No. 16/935,236 Office Action dated Jun. 16, 2022.
EP Application # 19877990.2 Search Report dated Jul. 5, 2022.
(Continued)

*Primary Examiner* — Mark W. Bockelman
(74) *Attorney, Agent, or Firm* — MEITAR PATENTS LTD.

(57) ABSTRACT

A system includes a radiation source and a controller. The controller is configured to designate, for irradiation, multiple target regions on an eye of a patient, and to perform an iterative process that includes, during each iteration of the process, acquiring an image of the eye, based on the image, calculating a location of a different respective one of the target regions, processing the image so as to identify any obstruction at the location, and provided no obstruction at the location is identified, causing the radiation source to irradiate the location. Other embodiments are also described.

12 Claims, 7 Drawing Sheets

Related U.S. Application Data

(60) Provisional application No. 62/692,868, filed on Jul. 2, 2018, provisional application No. 62/739,238, filed on Sep. 30, 2018, provisional application No. 62/748,461, filed on Oct. 21, 2018.

(52) U.S. Cl.
CPC .... *A61F 9/00823* (2013.01); *A61B 2090/049* (2016.02); *A61F 2009/00868* (2013.01); *A61F 2009/00891* (2013.01)

(58) Field of Classification Search
CPC ................. A61F 9/00821; A61B 90/04; A61B 2090/049
See application file for complete search history.

(56) References Cited

U.S. PATENT DOCUMENTS

| | | |
|---|---|---|
| 4,587,257 A | 5/1986 | DeSantis |
| 4,641,349 A | 2/1987 | Flom et al. |
| 4,718,418 A | 1/1988 | L'Esperance |
| 4,848,894 A | 7/1989 | Buser et al. |
| 4,941,093 A | 7/1990 | Marshall et al. |
| 4,966,452 A | 10/1990 | Shields et al. |
| 5,049,147 A | 9/1991 | Danon |
| 5,123,902 A | 6/1992 | Muller et al. |
| 5,141,506 A | 8/1992 | York |
| 5,151,909 A | 9/1992 | Davenport et al. |
| 5,152,760 A | 10/1992 | Latina |
| 5,370,641 A | 12/1994 | O'Donnell, Jr. |
| 5,422,899 A | 6/1995 | Freiberg et al. |
| 5,479,222 A | 12/1995 | Volk et al. |
| 5,549,596 A | 8/1996 | Latina |
| 5,598,007 A | 1/1997 | Bunce et al. |
| 5,786,883 A | 7/1998 | Miller et al. |
| 5,865,830 A | 2/1999 | Parel et al. |
| 5,982,789 A | 11/1999 | Marshall et al. |
| 6,027,216 A | 2/2000 | Guyton et al. |
| 6,033,396 A | 3/2000 | Huang et al. |
| 6,059,772 A | 5/2000 | Hsia et al. |
| 6,096,029 A | 8/2000 | O'Donnell, Jr. |
| 6,099,521 A | 8/2000 | Shadduck |
| 6,099,522 A | 8/2000 | Knopp et al. |
| 6,146,375 A | 11/2000 | Juhasz et al. |
| 6,210,399 B1 | 4/2001 | Parel et al. |
| 6,258,082 B1 | 7/2001 | Lin |
| 6,263,879 B1 | 7/2001 | Lin |
| 6,267,752 B1 | 7/2001 | Svetliza |
| 6,267,756 B1 | 7/2001 | Feuerstein et al. |
| 6,319,274 B1 | 11/2001 | Shadduck |
| 6,325,792 B1 | 12/2001 | Swinger et al. |
| 6,414,980 B1 | 7/2002 | Wang et al. |
| 6,454,763 B1 | 9/2002 | Motter et al. |
| 6,514,241 B1 | 2/2003 | Hsia et al. |
| 6,530,916 B1 | 3/2003 | Shimmick |
| 6,569,104 B2 | 5/2003 | Ono et al. |
| 6,673,062 B2 | 1/2004 | Yee et al. |
| 6,676,655 B2 | 1/2004 | McDaniel |
| 6,685,317 B2 | 2/2004 | Su et al. |
| 6,698,886 B2 | 3/2004 | Pollack et al. |
| 6,736,806 B2 | 5/2004 | Ruiz et al. |
| 6,761,713 B2 | 7/2004 | Teichmann |
| 6,899,707 B2 | 5/2005 | Scholler et al. |
| 6,942,656 B2 | 9/2005 | Pawlowski et al. |
| 6,948,815 B2 | 9/2005 | Neuberger |
| 6,979,328 B2 | 12/2005 | Baerveldt et al. |
| 7,027,233 B2 | 4/2006 | Goldstein et al. |
| 7,252,661 B2 | 8/2007 | Nguyen et al. |
| 7,282,046 B2 | 10/2007 | Simon |
| 7,353,829 B1 | 4/2008 | Wachter et al. |
| 7,371,230 B2 | 5/2008 | Webb et al. |
| 7,693,259 B2 | 4/2010 | Gertner |
| 7,792,249 B2 | 9/2010 | Gertner et al. |
| 8,004,764 B2 | 8/2011 | Artsyukhovich et al. |
| 8,048,065 B2 | 11/2011 | Grecu et al. |
| 8,109,635 B2 | 2/2012 | Allon et al. |
| 8,160,113 B2 | 4/2012 | Adams et al. |
| 8,403,921 B2 | 3/2013 | Palankar et al. |
| 8,442,185 B2 | 5/2013 | Gertner et al. |
| 8,465,478 B2 | 6/2013 | Frey et al. |
| 8,475,433 B2 | 7/2013 | Mrochen et al. |
| 8,545,020 B2 | 10/2013 | Liesfeld et al. |
| 8,568,393 B2 | 10/2013 | Palanker |
| 8,630,388 B2 | 1/2014 | Gertner et al. |
| 8,679,100 B2 | 3/2014 | Raksi et al. |
| 8,708,491 B2 | 4/2014 | Frey et al. |
| 8,709,029 B2 | 4/2014 | Griffis, III et al. |
| 8,771,261 B2 | 7/2014 | Andersen et al. |
| 8,811,657 B2 | 8/2014 | Teiwes et al. |
| 8,845,625 B2 | 9/2014 | Angeley et al. |
| 8,903,468 B2 | 12/2014 | Peyman |
| 8,920,407 B2 | 12/2014 | Raksi et al. |
| 8,939,965 B2 | 1/2015 | Liesfeld et al. |
| 8,968,279 B2 | 3/2015 | Arnoldussen |
| 8,995,618 B2 | 3/2015 | Gertner |
| 9,055,896 B2 | 6/2015 | Amthor et al. |
| 9,192,780 B2 | 11/2015 | McDaniel |
| 9,220,407 B2 | 12/2015 | Yam et al. |
| 9,351,878 B2 | 5/2016 | Muehlhoff et al. |
| 9,480,599 B2 | 11/2016 | Degani et al. |
| 9,495,743 B2 | 11/2016 | Angeley et al. |
| 9,504,609 B2 | 11/2016 | Kurtz |
| 9,532,712 B2 | 1/2017 | Liesfeld et al. |
| 9,622,911 B2 | 4/2017 | Rubinfeld et al. |
| 9,782,232 B1 | 10/2017 | Papac |
| 9,849,032 B2 | 12/2017 | Schuele et al. |
| 9,849,034 B2 | 12/2017 | Artsyukhovich et al. |
| 9,877,633 B2 | 1/2018 | Zhao et al. |
| 9,889,043 B2 | 2/2018 | Frey et al. |
| 9,968,483 B2 | 5/2018 | Takeda et al. |
| 10,022,457 B2 | 7/2018 | Peyman |
| 10,064,757 B2 | 9/2018 | Berlin |
| 10,143,590 B2 | 12/2018 | Dick et al. |
| 10,244,991 B2 | 4/2019 | Shademan et al. |
| 10,258,507 B2 | 4/2019 | Gonzalez et al. |
| 10,278,865 B2 | 5/2019 | Luttrull et al. |
| 10,299,961 B2 | 5/2019 | Luttrull et al. |
| 10,363,169 B2 | 7/2019 | Belkin et al. |
| 10,441,465 B2 | 10/2019 | Hart et al. |
| 10,449,091 B2 | 10/2019 | Angeley et al. |
| 10,456,209 B2 | 10/2019 | Peyman |
| 10,478,342 B2 | 11/2019 | Dick et al. |
| 10,524,656 B2 | 1/2020 | Wiltberger et al. |
| 10,617,564 B1 | 4/2020 | Andersen et al. |
| 10,684,449 B2 | 6/2020 | Curatu et al. |
| 10,702,416 B2 | 7/2020 | Belkin et al. |
| 10,849,789 B2 | 12/2020 | Dewey et al. |
| 10,925,768 B2 | 2/2021 | Charles |
| 2001/0027314 A1 | 10/2001 | Peyman |
| 2002/0013573 A1 | 1/2002 | Telfair et al. |
| 2003/0179344 A1 | 9/2003 | Van de Velde |
| 2003/0225398 A1 | 12/2003 | Zepkin et al. |
| 2004/0039378 A1 | 2/2004 | Lin |
| 2004/0059321 A1 | 3/2004 | Knopp et al. |
| 2005/0096639 A1 | 5/2005 | Slatkine et al. |
| 2005/0107774 A1 | 5/2005 | Lin |
| 2005/0185138 A1 | 8/2005 | Wong et al. |
| 2005/0197655 A1 | 9/2005 | Telfair et al. |
| 2005/0254009 A1 | 11/2005 | Baker et al. |
| 2005/0286019 A1 | 12/2005 | Wiltberger et al. |
| 2005/0288745 A1 | 12/2005 | Andersen et al. |
| 2006/0100677 A1 | 5/2006 | Blumenkranz et al. |
| 2006/0176913 A1 | 8/2006 | Souhaite et al. |
| 2006/0195076 A1 | 8/2006 | Blumenkranz et al. |
| 2006/0265030 A1 | 11/2006 | McDaniel |
| 2007/0081166 A1 | 4/2007 | Brown et al. |
| 2007/0129709 A1 | 6/2007 | Andersen et al. |
| 2007/0159600 A1 | 7/2007 | Gil et al. |
| 2007/0213693 A1 | 9/2007 | Plunkett |
| 2008/0089481 A1 | 4/2008 | Gertner |
| 2008/0108934 A1 | 5/2008 | Berlin et al. |
| 2008/0161781 A1 | 7/2008 | McArdle et al. |
| 2008/0167642 A1 | 7/2008 | Palanker et al. |
| 2008/0204658 A1 | 8/2008 | Van Saarloos |

(56) References Cited

U.S. PATENT DOCUMENTS

| | | |
|---|---|---|
| 2008/0234667 A1 | 9/2008 | Lang et al. |
| 2008/0255546 A1 | 10/2008 | Orbachevski |
| 2009/0093798 A1* | 4/2009 | Charles ............... A61F 9/00823 606/4 |
| 2009/0137993 A1 | 5/2009 | Kurtz |
| 2009/0157062 A1 | 6/2009 | Hauger et al. |
| 2009/0247997 A1 | 10/2009 | Watanabe et al. |
| 2010/0002837 A1 | 1/2010 | Gertner et al. |
| 2010/0057059 A1 | 3/2010 | Makino |
| 2010/0076419 A1 | 3/2010 | Chew et al. |
| 2010/0142767 A1 | 6/2010 | Fleming |
| 2010/0324543 A1 | 12/2010 | Kurtz et al. |
| 2011/0144627 A1 | 6/2011 | Smith et al. |
| 2011/0172649 A1 | 7/2011 | Schuele et al. |
| 2011/0190741 A1 | 8/2011 | Deisinger et al. |
| 2012/0016349 A1 | 1/2012 | Brownell |
| 2012/0050308 A1 | 3/2012 | Nakano et al. |
| 2012/0083772 A1 | 4/2012 | Rubinfeld et al. |
| 2012/0089134 A1 | 4/2012 | Horvath et al. |
| 2012/0259321 A1 | 10/2012 | Vera et al. |
| 2012/0283557 A1 | 11/2012 | Berlin |
| 2013/0103011 A1 | 4/2013 | Grant et al. |
| 2013/0123761 A1 | 5/2013 | Belkin et al. |
| 2013/0204236 A1 | 8/2013 | Awdeh |
| 2013/0218145 A1 | 8/2013 | Belkin et al. |
| 2013/0289450 A1 | 10/2013 | Homer |
| 2013/0317570 A1 | 11/2013 | Luttrull et al. |
| 2014/0094785 A1 | 4/2014 | Charles |
| 2014/0114297 A1 | 4/2014 | Woodley et al. |
| 2014/0128731 A1 | 5/2014 | Gonzalez et al. |
| 2014/0128851 A1 | 5/2014 | Wysopal |
| 2014/0128852 A1 | 5/2014 | Gooding et al. |
| 2014/0135747 A1 | 5/2014 | Donitzky et al. |
| 2014/0135753 A1 | 5/2014 | Feklistov et al. |
| 2014/0276681 A1 | 9/2014 | Schuele et al. |
| 2014/0307077 A1 | 10/2014 | Prabhakar |
| 2015/0164635 A1 | 6/2015 | Renke |
| 2015/0223683 A1 | 8/2015 | Davidovics et al. |
| 2015/0266706 A1 | 9/2015 | Hashimoto |
| 2015/0272782 A1 | 10/2015 | Schuele et al. |
| 2015/0313759 A1 | 11/2015 | Vera et al. |
| 2016/0008169 A1 | 1/2016 | Yu |
| 2016/0008172 A1 | 1/2016 | Kahook |
| 2016/0067087 A1 | 3/2016 | Tedford et al. |
| 2016/0089269 A1 | 3/2016 | Horvath et al. |
| 2016/0095752 A1 | 4/2016 | Srinivasan et al. |
| 2016/0113816 A1 | 4/2016 | Herekar et al. |
| 2016/0346126 A1 | 12/2016 | Luttrull et al. |
| 2016/0354241 A1 | 12/2016 | Mordaunt et al. |
| 2016/0367399 A1 | 12/2016 | Goldshleger et al. |
| 2017/0038284 A1 | 2/2017 | Nemati |
| 2017/0087014 A1 | 3/2017 | Potter, Jr. et al. |
| 2017/0127938 A1 | 5/2017 | Izatt et al. |
| 2017/0184875 A1 | 6/2017 | Newman |
| 2017/0246033 A1 | 8/2017 | Bor et al. |
| 2017/0340483 A1 | 11/2017 | Rill et al. |
| 2017/0360604 A1 | 12/2017 | Bach et al. |
| 2018/0085257 A1 | 3/2018 | Horvath et al. |
| 2018/0104477 A1 | 4/2018 | Kurtz et al. |
| 2018/0125708 A1 | 5/2018 | Bohme et al. |
| 2018/0168737 A1 | 6/2018 | Ren et al. |
| 2018/0207029 A1 | 7/2018 | Herekar et al. |
| 2018/0214305 A1 | 8/2018 | Schuele et al. |
| 2018/0221199 A1 | 8/2018 | Heacock |
| 2018/0235462 A1 | 8/2018 | Gooi et al. |
| 2018/0344527 A1 | 12/2018 | Palanker et al. |
| 2019/0078073 A1 | 3/2019 | Streeter et al. |
| 2019/0099291 A1 | 4/2019 | Herekar et al. |
| 2019/0105200 A1 | 4/2019 | Hipsley |
| 2019/0105519 A1 | 4/2019 | Herekar et al. |
| 2019/0117459 A1 | 4/2019 | Berlin |
| 2019/0142636 A1 | 5/2019 | Tedford et al. |
| 2019/0151146 A1 | 5/2019 | Kim |
| 2019/0247225 A1 | 8/2019 | Stobrawa et al. |
| 2019/0269554 A1 | 9/2019 | Goldshleger et al. |
| 2019/0343680 A1 | 11/2019 | Belkin et al. |
| 2019/0344076 A1 | 11/2019 | Irazoqui et al. |
| 2019/0358085 A1 | 11/2019 | Fu et al. |
| 2020/0038245 A1 | 2/2020 | Hart et al. |
| 2020/0078216 A1 | 3/2020 | Raksi |
| 2020/0093639 A1 | 3/2020 | McCall, Jr. |
| 2020/0107724 A1 | 4/2020 | Wiltberger et al. |
| 2020/0146887 A1 | 5/2020 | Horvath et al. |
| 2020/0306080 A1 | 10/2020 | Herekar et al. |
| 2020/0345546 A1 | 11/2020 | Belkin et al. |
| 2020/0352785 A1 | 11/2020 | Holland et al. |
| 2020/0360187 A1 | 11/2020 | Schuele et al. |
| 2020/0379216 A1 | 12/2020 | Curatu et al. |
| 2021/0338484 A1 | 11/2021 | Hipsley |
| 2023/0201037 A1 | 6/2023 | Barrett et al. |
| 2023/0226372 A1 | 7/2023 | Herekar et al. |

FOREIGN PATENT DOCUMENTS

| | | |
|---|---|---|
| CA | 2640203 A1 | 8/2007 |
| CN | 1579351 A | 2/2005 |
| CN | 101411607 A | 4/2009 |
| CN | 201537172 U | 8/2010 |
| CN | 102193182 A | 9/2011 |
| CN | 105138996 A | 12/2015 |
| CN | 205698218 U | 11/2016 |
| DE | 202016006265 U1 | 3/2017 |
| EP | 0224322 A1 | 6/1987 |
| EP | 0651982 A1 | 5/1995 |
| EP | 0689811 A1 | 1/1996 |
| EP | 1602321 A1 | 12/2005 |
| EP | 2301421 A1 | 3/2011 |
| EP | 2301424 B1 | 3/2011 |
| EP | 2301425 B1 | 3/2011 |
| EP | 2602005 A1 | 6/2013 |
| EP | 1856774 B1 | 6/2016 |
| EP | 2695016 B1 | 3/2017 |
| EP | 2992931 B1 | 8/2017 |
| EP | 2391318 B1 | 12/2017 |
| EP | 3329839 A1 | 6/2018 |
| EP | 2729099 B1 | 11/2019 |
| EP | 3191040 B1 | 7/2020 |
| EP | 3517081 B1 | 11/2020 |
| EP | 2854729 B1 | 3/2021 |
| FR | 2655837 A1 | 6/1991 |
| JP | 2007151739 A | 6/2007 |
| JP | 2010148635 A | 7/2010 |
| JP | 2016013255 A | 1/2016 |
| JP | 2018051210 A | 4/2018 |
| KR | 20180106113 A | 10/2018 |
| KR | 20190022216 A | 3/2019 |
| RU | 2499582 C1 | 11/2013 |
| RU | 2553507 C1 | 6/2015 |
| WO | 9216259 A1 | 10/1992 |
| WO | 1993012727 A1 | 7/1993 |
| WO | 9316631 A1 | 9/1993 |
| WO | 9412092 A1 | 6/1994 |
| WO | 9416425 A1 | 7/1994 |
| WO | 9515134 A1 | 6/1995 |
| WO | 1998022016 A2 | 5/1998 |
| WO | 9918868 A1 | 4/1999 |
| WO | 0195842 A1 | 12/2001 |
| WO | 02064031 A2 | 8/2002 |
| WO | 02087442 A1 | 11/2002 |
| WO | 2014018104 A1 | 1/2004 |
| WO | 2004027487 A1 | 4/2004 |
| WO | 2006119349 A2 | 11/2006 |
| WO | 2006119584 A1 | 11/2006 |
| WO | 2006128038 A2 | 11/2006 |
| WO | 2007103349 A2 | 9/2007 |
| WO | 2008112236 A1 | 9/2008 |
| WO | 2008118198 A2 | 10/2008 |
| WO | 2010094353 A1 | 8/2010 |
| WO | 2010113193 A1 | 10/2010 |
| WO | 2011017002 A2 | 2/2011 |
| WO | 2011163508 A2 | 6/2011 |
| WO | 2011085274 A1 | 7/2011 |
| WO | 2011151812 A1 | 12/2011 |
| WO | 2013004255 A1 | 1/2013 |

(56) References Cited

FOREIGN PATENT DOCUMENTS

| | | |
|---|---|---|
| WO | 2013035091 A1 | 3/2013 |
| WO | 2013059481 A1 | 4/2013 |
| WO | 2013059564 A1 | 4/2013 |
| WO | 2013122711 A1 | 8/2013 |
| WO | 2013165689 A1 | 11/2013 |
| WO | 2014025862 A1 | 2/2014 |
| WO | 2014132162 A1 | 9/2014 |
| WO | 2014191031 A1 | 12/2014 |
| WO | 2015069197 A1 | 5/2015 |
| WO | 2015130821 A2 | 9/2015 |
| WO | 2016018864 A1 | 2/2016 |
| WO | 2016058931 A2 | 4/2016 |
| WO | 2016156760 A1 | 10/2016 |
| WO | 2016187436 A1 | 11/2016 |
| WO | 2016207739 A1 | 12/2016 |
| WO | 2017023296 A1 | 2/2017 |
| WO | 2017031570 A1 | 3/2017 |
| WO | 2017069819 A1 | 4/2017 |
| WO | 2018005796 A1 | 1/2018 |
| WO | 2018021780 A1 | 2/2018 |
| WO | 2018049246 A1 | 3/2018 |
| WO | 2018152020 A1 | 8/2018 |
| WO | 2018232397 A1 | 12/2018 |
| WO | 2019109125 A1 | 6/2019 |
| WO | 2020008323 A1 | 1/2020 |
| WO | 2020012841 A1 | 1/2020 |
| WO | 2020018242 A1 | 1/2020 |
| WO | 2020018436 A1 | 1/2020 |
| WO | 2020050308 A1 | 3/2020 |
| WO | 202093060 A2 | 5/2020 |
| WO | 2020089737 A1 | 5/2020 |
| WO | 2020183342 A1 | 9/2020 |
| WO | 2021026538 A1 | 2/2021 |
| WO | 2021048723 A1 | 3/2021 |
| WO | 2021155445 A1 | 8/2021 |
| WO | 2021170664 A1 | 9/2021 |
| WO | 2022223690 A1 | 10/2022 |

OTHER PUBLICATIONS

Nagar et al., "A randomised, prospective study comparing selective laser trabeculoplasty with latanoprost for the control of intraocular pressure in ocular hypertension and open angle glaucoma," British Journal of Ophthalmology, vol. 89, pp. 1413-1417, year 2005.
Hong et al., "Repeat Selective Laser Trabeculoplasty," Journal of Glaucoma, vol. 18, issue 3, pp. 180-183, Mar. 2009.
Goyal et al., "Effect of primary selective laser trabeculoplasty on tonographic outflow facility—a randomised clinical trial," British Journal of Ophthalmology, BMJ Publishing Group, vol. 94, issue 11, pp. 1-22, year 2010.
Franco et al., "Effect of Second SLT on IOP," Investigative Ophthalmology & Visual Science, vol. 48, pp. May 1-2, 2007.
Chen et al., "A Comparison between 90 degrees and 180 degrees Selective Laser Trabeculoplasty," Journal of Glaucoma, vol. 13, issue 1, p. 1, Feb. 2004.
Mequio et al, "Efficacy of Repeat Selective Laser Trabeculoplasty," Investigative Ophthalmology & Visual Science, vol. 48, p. 1, year 2007.
Grulkowski et al., "Anterior segment imaging with Spectral OCT system using a high-speed CMOS camera," Optics Express, vol. 17, No. 6, p. 4842-4858, year 2009.
Shields et al., "Noncontact Transscleral ND:YAG Cyclophotocoagulation: A Long-Term Follow-Up of 500 Patients," Transactions of the American Ophthalmological Society, vol. XCII, pp. 271-287, year 1994.
Liu et al., "Real-time visual analysis of microvascular blood flow for critical care," CVPR2015 paper as Open Access Version, provided by the Computer Vision Foundation, pp. 2217-2225, year 2015.
Desco et al., "Effect of prophylactic brimonidine on bleeding complications after cataract surgery," European Journal of Ophthalmology, vol. 15, pp. 228-232, year 2005.

Pasquali et al., "Dilute brimonidine to improve patient comfort and subconjunctival hemorrhage after LASIK," Journal of Refractive Surgery, vol. 29, pp. 469-475, year 2013.
Sacks et al., "Non-contact direct selective laser trabeculoplasty: light propagation analysis," Biomedical Optics Express, vol. 11, pp. 2889-2904, year 2020.
Kasuga et al., "Trabecular Meshwork Length in Men and Women by Histological Assessment," Current Eye Research, Early Online, pp. 1-5, Jun. 2012.
International Application # PCT/IB2020/058300 Search Report dated Dec. 27, 2020.
SensoMotoric Instruments GmbH (SMI), "SG 3000", Product Flyer, pp. 1-2, year 2010.
Ashik et al., "The precision of ophthalmic biometry using calipers," Canadian Journal of Ophthalmology, vol. 48, Issue 6, pp. 1-13, Dec. 2013.
Balalzsi, "Noncontact Thermal Mode Nd:YAG Laser Transscleral Cyclocoagulation in the Treatment of Glaucoma," Ophthalmology, vol. 98, pp. 1858-1863, year 1991.
Leung et al., "Anterior chamber angle imaging with optical coherence tomography," Eye, vol. 25, pp. 261-267, year 2011.
Tasman et al., "The Wills Eye Hospital Atlas of Clinical Ophthalmology," Lippincott Williams & Wilkins, p. 158, year 2001.
Gaasterland, "Laser Therapies: Iridotomy, Iridoplasty, and Trabeculoplasty," as appears in "The Glaucoma Book: A Practical Evidence-Based Approach to Patient Care," Springer, p. 722, year 2010.
Kara, "Bleeding in Retinal Images Using Image Processing", A Thesis submitted to the graduate school of applied sciences of Near East University, pp. 1-79, Nicosia, Larnaca, year 2019.
Navilas Operator Manual, Document Version 2.10, 2012 OD-OS GmbH, pp. 1-94, Sep. 2012.
Vogel et al., "Optical properties of humn sclera, and their consequences for transscleral laser applications.", Lasers In Surgery and Medicine , vol. 11, pp. 331-340, 1991.
Geffen et al., "Transscleral Selective Laser Trabeculoplasty Without a Gonioscopy Lens", Journal of Glaucoma, Inc, vol. 26, No. 3, pp. 201-207, Mar. 2017.
Das et al., "Sclera Recognition—A Survey", 2nd IAPR Asian Conference on Pattern Recognition, pp. 1-5, Naha, Japan, Nov. 5-8, 2013.
Kaya et al., "Designing a Pattern Stabilization Method Using Scleral Blood Vessels for Laser Eye Surgery", International Conference on Pattern Recognition, pp. 698-701, Istanbul, Turkey, Aug. 23-26, 2010.
International Application # PCT/IB2019/055564 search report dated Oct. 10, 2019.
Arany, "Photobiomodulation therapy: Easy to do, but difficult to get right", LaserFocusWorld, pp. 1-6, Jul. 31, 2019 downloaded from www.laserfocusworld.com/lasers-sources/article/14037967/photobiomodulation-therapyeasy-to-do-but-difficult-to-get-right, pp. 22-24, year 2019.
Borzabadi-Farahani, "Effect of low-level laser irradiation on proliferation of human dental mesenchymal stem cells; a systemic review", Journal of Photochemistry and Photobiology B: Biology, vol. 162, pp. 577-582, Sep. 2016.
Ascott et al., "Trabecular Repopulation by Anterior Trabecular Meshwork Cells After Laser Trabeculoplasty", American Journal of Ophthalmology, vol. 107, issue 1, pp. 1-6, Jan. 1989.
Cao et al., "Peripheral Iridotomy," Medscape 25, pp. 1-12, Jun. 15, 2020.
Husain, "Laser Peripheral Iridotomy—Practical Points", YouTube presentation, p. 1, Sep. 28, 2016, downloaded from https://www.youtube.com/watch?=Azxzsv31yls.
Ivandic et al., "Early Diagnosis of Ocular Hypertension Using a Low-Intensity Laser Irradiation Test", Photomedicine and Laser Surgey, vol. 00, No. 00, pp. 1-5, year 2009.
Smith et al., "Light scatter from the central human cornea", Journal "Eye", issue 4, pp. 584-588, year 1990.
Turati et al., "Patterned Laser Trabeculoplasty", Ophthalmic Surgery, Lasers and Imaging , vol. 41, No. 5, pp. 538-545, 2010.

(56) References Cited

OTHER PUBLICATIONS

Nozaki et al.,"Patterned Laser Trabeculoplasty with PASCAL streamline 577", Investigative Ophthalmology & Visual Science, vol. 54, p. 1867, Jun. 2013.
Barkana et al., "Selective Laser Trabeculoplasty", Survey of Ophthalmology, vol. 52, No. 6, pp. 634-653, year 2007.
AU Application # 2019297135 Office Action dated Sep. 30, 2021.
International Application # PCT/IB2021/054187 Search Report dated Jul. 30, 2021.
U.S. Appl. No. 16/420,194 Office Action dated Jul. 22, 2021.
EP Application # 20201567.3 Search Report dated Jun. 22, 2021.
CN Application # 2020800163407 Office Action dated Feb. 4, 2023.
JP Application # 2020561860 Office Action dated Feb. 7, 2023.
U.S. Appl. No. 17/254,279 Office Action dated Dec. 20, 2021.
AU Application # 2019297135 Office Action dated Jan. 5, 2022.
U.S. Appl. No. 16/935,236 Office Action dated Jan. 6, 2022.
IN Application # 202147003401 Office Action dated Jan. 13, 2022.
CN Application # 201980043641.6 Office Action dated Feb. 18, 2022.
EP Application # 19830473.5 Search Report dated Feb. 28, 2022.
IN Application # 201948052117 Office Action dated Feb. 16, 2022.
Katta et al., "Optical Coherence Tomography Image-Guided Smart Laser Knife for Surgery," Lasers in Surgery and Medicine, Wiley Online Library, pp. 1-11, Jul. 2017.
Barnes et al., "Control of Intraocular Pressure Elevations after Argon Laser Trabeculoplasty: Comparison of Brimonidine 0.2% to Apraclonidine 1.0%," Opthalmology, vol. 106, No. 10, pp. 2033-2037, year 1999.
Yakopson et al., "Brimonidine 0.1% vs. Apraclonidine 0.5% for Prevention of Intraocular Pressure Elevation after Selective Laser Trabeculoplasty," Investigative Ophthalmology & Visual Science, vol. 49, p. 1234, May 2008.
Kim et at., "Effect of Prophylactic Topical Brimonidine (0.15%) Administration on the Development of Subconjunctival Hemorrhage after Intravitreal Injection," Retina, The Journal for Retinal and Vitreous Diseases, vol. 31, No. 2, pp. 389-392, year 2011.
Hong et al., "Effect of Prophylactic Brimonidine Instillation on Bleeding during Strabismus Surgery in Adults," American Journal of Ophthalmology, vol. 144, No. 3, pp. 469-470, Sep. 2007.
Goldsmith et al., "Anterior Chamber Width Measurement by High-Speed Optical Coherence Tomography," Ophthalmology, vol. 112, No. 2, pp. 238-244, year 2005.
Norden, "Effect of Prophilactic Brimonidine on Bleeding Complications and Flap Adherence After Laser in situ Keratomileusis," Journal of Refractive Surgery, vol. 18, No. 4, pp. 468-471, Jul./Aug. 2002.
Kohnen et al., "Internal Anterior Chamber Diameter using Optical Coherence Tomography Compared with White-to-White Distances using Automated Measurements," Journal of Cataract & Refractive Surgery, vol. 32, pp. 1809-1813, Nov. 2006.
Zhang et al., "Perioperative Medications for Preventing Temporarily Increased Intraocular Pressure after Laser Trabeculoplasty (Review)," Cochrane Database of Systematic Reviews 2017, issue 2, pp. 1-117, year 2017.
Gophotonics, "NL200 series," Data Sheet, pp. 1-3, Jun. 29, 2017.
EP Application # 20201567.3 Office Action dated Jun. 6, 2023.
JP Application # 2020561860 Office Action dated Jun. 13, 2023.
JP Application # 2021516473 Office Action dated Jun. 20, 2023.
CN Application # 2020800563096 Office Action dated Jul. 1, 2023.
EP Application # 20864109.2 Search Report dated Aug. 10, 2023.
Pinnamaneni et al., "Concise Review: Stem Cells in the Corneal Stroma," Stem Cells, vol. 30, issue 6, pp. 1059-1063, year 2012.
Walshe et al., "Serial Explant Culture Provides Novel Insights into the Potential Location and Phenotype of Corneal Endothelial Progenitor Cells," Experimental Eye Research, vol. 127, pp. 9-13, year 2014.
Espana et al., "Existence of Corneal Endothelial Slow-Cycling Cells," Investigative Ophthalmology & Visual Science, vol. 56, No. 6, pp. 3827-3837, Jun. 2015.
Sepehr, "Corneal Endothelial Cell Dysfunction: Etiologies and Management," Therapeutic Advances in Opthalmology, pp. 1-19, year 2018.
Gonzalez et al., "Limbal Stem Cells: Identity, Developmental Origin, and Therapeutic Potential," WIREs Developmental Biology, Wiley, vol. 7, issue 2, pp. 1-23, Mar. 2018.
Kim et al., "Diagnosis of Corneal Limbal Stem Cell Deficiency," Current Opinion in Ophthalmology, Wolters Kluwer Health, Inc., vol. 28, No. 4, pp. 355-362, Jul. 2017.
Nowell et al., "Corneal Epithelial Stem Cells and their Niche at a Glance," Cell Science at a Glance, vol. 130, Issue 6, pp. 1021-1025, year 2017.
Dueker et al., "Stimulation of Cell Division by Argon and Nd:YAG Laser Trabeculoplasty in Cynomolgus Monkeys," Investigative Ophthalmology & Visual Science, vol. 31, No. 1, pp. 115-124, year 1990.
Kelley et al., "Stem Cells in the Trabecular Meshwork: Present and Future Promises," Experimental Eye Research, vol. 88, issue 4, pp. 747-751, Apr. 2009.
Gazzard et al., "Selective Laser Trabeculoplasty versus Drops for Newly Diagnosed Ocular Hypertension and Glaucoma: The LiGHT RCT," Health Technology Assessment, NHS, vol. 23, issue 31, pp. 1-132, Jun. 2019.
CN Application # 2019800436416 Office Action dated Aug. 17, 2022.
U.S. Appl. No. 16/935,236 Office Action dated Sep. 15, 2022.
U.S. Appl. No. 16/420,194 Office Action dated Aug. 5, 2022.
U.S. Appl. No. 16/935,236 Office Action dated Nov. 7, 2022.
EP Application # 20769533.9 Search Report dated Nov. 8, 2022.
AU Application # 2020345067 Office Action dated Nov. 30, 2022.
CN Application # 201980070459X Office Action dated Dec. 23, 2022.
"Smart Selecta Duet—Your Smart Selection for Glaucoma Care," Product Brochure, pp. 1-6, The Lumenis Group of Companies, year 2018.
Root, "How to perform a Laser Iridotomy (Video)," pp. 1-14, year 2010, as downloaded from https://timroot.com/how-to-perform-a-laser-iridotomy-video/.
AU Application # 2022211843 Office Action dated Sep. 27, 2023.
AU Application # 2021311097 Office Action dated Sep. 28, 2023.
U.S. Appl. No. 17/427,926 Office Action dated Oct. 17, 2023.
JP Application # 2021536316 Office Action dated Oct. 24, 2023.
JP Application # 2020561860 Office Action dated Oct. 31, 2023.
JP Application # 2021516473 Office Action dated Nov. 7, 2023.
SG Application # 11202010437T Office Action Dec. 5, 2023.
U.S. Appl. No. 17/735,153 Office Action dated Dec. 18, 2023.
International Application # PCT/IB2023/060104 Search Report Dec. 26, 2023.
U.S. Appl. No. 17/427,926 Office Action dated Dec. 22, 2023.
Danielson et al., Fixed High-Energy versus Standard Titrated Energy Settings for Selective Laser Trabeculoplasty, Journal of Glaucoma Publish Ahead of Print, Wolters Kluwer Health, Inc., pp. 1-16, year 2023.
Radcliffe et al., "Energy Dose-Response in Selective Laser Trabeculoplasty: A Review," Journal of Glaucoma, vol. 31, pp. e49-e68, year 2022.
Gazzard, "A Brief Guide to Gonioscopy," Video Clip, Optometry today, pp. 1-2, May 21, 2015, as downloaded from https://www.youtube.com/watch?v=8yTTbHWxUik.
Alward et al., "Principles of Gonioscopy," Color Atlas of Gonioscopy, American Academy of Opthalmology, pp. 1-10, Nov. 8, 2017, as downloaded from https://www.aao.org/education/disease-review/principles-of-gonioscopy.
Nolan et al., "Gonioscopy skills and techniques," Community Eye Health Journal, vol. 34, No. 112, pp. 40-42, year 2021.
Breazzano et al., "Analysis of Schwalbe's Line (Limbal Smooth Zone) by Scanning Electron Microscopy and Optical Coherence Tomography in Human Eye Bank Eyes," Journal of Ophthalmic and Vision Research, vol. 8, issue 1, pp. 9-16, Jan. 2013.
Thorlabs, Inc., "CPS520—Collimated Laser Diode Module, 520 nm, 4.5 mW, Elliptical Beam, Ø11 mm," Product Details, pp. 1-1, years 1999-2023, as downloaded from https://www.thorlabs.com/thorproduct.cfm?partnumber=CPS520.

(56) References Cited

OTHER PUBLICATIONS

Prophotonix, "Green Laser Modules," Product Information, pp. 1-8, year 2024, as downloaded from https://www.prophotonix.com/led-and-laser-products/laser-modules/laser-modules-color/green-laser-modules/.

Idex Helath & Science LLC, "532 nm StopLine® single-notch filter," Product Details, pp. 1-2, year 2023 as downloaded from https://www.idex-hs.com/store/product-detail/nf03_532e_25/fl-009362?cat_id=products&node=individual_optical_filters.

Brackley et al., "Lecture: Using the Slit Lamp Microscope to Visualize the Ocular Structures," Video Clip, pp. 1-2, Sep. 17, 2022, as downloaded from https://www.youtube.com/watch?v=1E-sEhy9tBo.

Bruce et al., "Zoom in on Gonioscopy," Review of Optometry, pp. 1-8, Sep. 1, 2016, as downloaded from https://www.reviewofoptometry.com/article/zoom-in-on-gonioscopy.

AU Application # 2022211843 Office Action dated Jan. 8, 2024.
JP Application # 2022508451 Office Action dated Mar. 5, 2024.
AU Application # 2021369792 Office Action dated Mar. 21, 2024.
International Application # PCT/IB2023/061472 Search Report dated Feb. 29, 2024.
U.S. Appl. No. 17/427,926 Office Action dated May 9, 2024.
EP Application # 19877990.2 Office Oction dated May 13, 2024.
EP Application # 24158977.9 Search Report dated May 15, 2024.
EP Applicatian # 21845437.9 Search Report dated Jun. 19, 2024.
JP Application # 2023217477 Office Action dated Jul. 9, 2024.
U.S. Appl. No. 17/273,323 Office Action dated Jun. 18, 2024.
EP Application 21885460.2 Search report dated Aug. 26, 2024.

\* cited by examiner

AVOIDING BLOOD VESSELS DURING DIRECT SELECTIVE LASER TRABECULOPLASTY

CROSS-REFERENCE TO RELATED APPLICATIONS

The present application is a continuation-in-part of International Patent Application PCT/IB2019/055564, published as WO/2020/008323, which claims the benefit of (i) U.S. Provisional Appl. No. 62/692,868, entitled "Direct laser selective trabeculoplasty Process (DSLT) and Safeties," filed Jul. 2, 2018, (ii) U.S. Provisional Appl. No. 62/739,238, entitled "Eye tracking flash illumination," filed Sep. 30, 2018, and (iii) U.S. Provisional Appl. No. 62/748,461, entitled "Crossed ranging beams," filed Oct. 21, 2018. The respective disclosure of each of the aforementioned references is incorporated herein by reference.

FIELD OF THE INVENTION

The present invention relates to ophthalmological devices and methods for the treatment of glaucoma, ocular hypertension (OHT), and other diseases.

BACKGROUND

In a trabeculoplasty procedure, a radiation source irradiates the trabecular meshwork in an eye of a patient with one or more treatment beams, thus lowering the intraocular pressure in the eye.

SUMMARY OF THE INVENTION

There is provided, in accordance with some embodiments of the present invention, a system including a radiation source and a controller. The controller is configured to designate, for irradiation, multiple target regions on an eye of a patient. The controller is further configured to perform an iterative process that includes, during each iteration of the process, acquiring an image of the eye, based on the image, calculating a location of a different respective one of the target regions, processing the image so as to identify any obstruction at the location, and provided no obstruction at the location is identified, causing the radiation source to irradiate the location.

In some embodiments, the process further includes, during at least one iteration of the process:
by processing the image, identifying an obstruction at the location, and
in response to identifying the obstruction, refraining from causing the radiation source to irradiate the location.

In some embodiments, refraining from causing the radiation source to irradiate the location includes causing the radiation source to irradiate another location instead of the location.

In some embodiments, refraining from causing the radiation source to irradiate the location includes terminating the iteration without causing the radiation source to irradiate any portion of the eye during the iteration.

In some embodiments, the obstruction includes a blood vessel.

In some embodiments,
the controller is configured to designate the multiple target regions for irradiation with respective amounts of energy, and
the process further includes, during at least one iteration of the process:
by processing the image, identifying an obstruction at the location, and
in response to identifying the obstruction, causing the radiation source to irradiate the location with another amount of energy that is less than the amount of energy designated for the target region.

There is further provided, in accordance with some embodiments of the present invention, a method including designating, for irradiation, multiple target regions on an eye of a patient. The method further includes performing an iterative process that includes, during each iteration of the process, acquiring an image of the eye, based on the image, calculating a location of a different respective one of the target regions, processing the image so as to identify any obstruction at the location, and provided no obstruction at the location is identified, causing a radiation source to irradiate the location.

There is further provided, in accordance with some embodiments of the present invention, a system including a radiation source and a controller. The controller is configured to designate multiple target regions on an eye of a patient for irradiation with respective amounts of energy. The controller is further configured to cause a radiation source to irradiate at least a first one of the target regions. The controller is further configured to identify a change in the eye, subsequently to causing the radiation source to irradiate at least the first one of the target regions, by processing an image of the eye. The controller is further configured to refrain from causing the radiation source to irradiate a second one of the target regions, which has not yet been irradiated, with the amount of energy designated for the second one of the target regions, in response to identifying the change.

In some embodiments, the controller is configured to refrain from causing the radiation source to irradiate the second one of the target regions by:
designating a new target region, and
causing the radiation source to irradiate the new target region instead of the second one of the target regions.

In some embodiments, the controller is configured to refrain from causing the radiation source to irradiate the second one of the target regions with the amount of energy designated for the second one of the target regions by causing the radiation source to irradiate the second one of the target regions with another amount of energy that is less than the designated amount.

In some embodiments, the change includes bleeding.
In some embodiments, the change includes swelling.
In some embodiments, the change includes a change in color.

In some embodiments, the controller is configured to refrain from causing the radiation source to irradiate the second one of the target regions in response to a distance between the second one of the target regions and another region of the eye.

In some embodiments,
the controller is further configured to identify an anatomical feature at the second one of the target regions, and
the controller is configured to refrain from causing the radiation source to irradiate the second one of the target regions in response to identifying the anatomical feature.

In some embodiments,
the controller is further configured to calculate a predicted measure of overlap between a radiation beam irradiating the second one of the target regions and the anatomical feature, and
the controller is configured to refrain from causing the radiation source to irradiate the second one of the target regions in response to the predicted measure of overlap.

In some embodiments,
the anatomical feature is a second-target-region anatomical feature,
the controller is further configured to identify a first-target-region anatomical feature at the first one of the target regions, and
the controller is configured to refrain from causing the radiation source to irradiate the second one of the target regions in response to identifying the first-target-region anatomical feature.

In some embodiments, the controller is configured to refrain from causing the radiation source to irradiate the second one of the target regions in response to the first-target-region anatomical feature and the second-target-region anatomical feature being of the same type.

In some embodiments,
the controller is further configured to:
    calculate an estimated measure of overlap between (a) a first radiation beam that irradiated the first one of the target regions and (b) the first-target-region anatomical feature, and
    calculate a predicted measure of overlap between (a) a second radiation beam irradiating the second one of the target regions and (b) the first-target-region anatomical feature, and
the controller is configured to refrain from causing the radiation source to irradiate the second one of the target regions in response to the predicted measure of overlap and the estimated measure of overlap.

In some embodiments,
the controller is further configured to:
    calculate an estimated amount of energy delivered by a first radiation beam to the first-target-region anatomical feature, and
    calculate a predicted amount of energy delivered by a second radiation beam to the second-target-region anatomical feature, and
the controller is configured to refrain from causing the radiation source to irradiate the second one of the target regions in response to the predicted amount of energy and the estimated amount of energy.

In some embodiments,
the controller is further configured to calculate a risk measure associated with irradiating the second one of the target regions, and
the controller is configured to refrain from causing the radiation source to irradiate the second one of the target regions in response to the risk measure.

In some embodiments, the controller is configured to calculate the risk measure based on a medical profile of the patient.

In some embodiments,
the controller is further configured to identify an anatomical feature at the second one of the target regions, and
the controller is configured to calculate the risk measure based on a type of the second anatomical feature.

There is further provided, in accordance with some embodiments of the present invention, a method including designating multiple target regions on an eye of a patient for irradiation with respective amounts of energy. The method further includes causing a radiation source to irradiate at least a first one of the target regions. The method further includes, subsequently to causing the radiation source to irradiate at least the first one of the target regions, by processing an image of the eye, identifying a change in the eye. The method further includes, in response to identifying the change, refraining from causing the radiation source to irradiate a second one of the target regions, which has not yet been irradiated, with the amount of energy designated for the second one of the target regions.

There is further provided, in accordance with some embodiments of the present invention, a system, including a radiation source and a controller. The controller is configured to acquire an image of an eye, to identify, in the image, multiple edge points at different respective angles relative to a reference point located on the eye radially inward from the edge points, each of the edge points lying on an edge of a respective blood vessel, to define multiple target regions on the eye between the reference point and the edge points, and to cause the radiation source to irradiate the target regions.

In some embodiments, the reference point is located at a center of an iris of the eye.

In some embodiments, the reference point is located at a center of a limbus of the eye.

In some embodiments, the reference point is located at a center of a pupil of the eye.

In some embodiments, for each angle, the edge of the respective blood vessel is closer to the reference point than is any other edge of any blood vessel at the angle.

In some embodiments, the controller is configured to define the target regions by:
    defining at least one treatment path between the edge points and the reference point, and
    defining the target regions such that each of the target regions lies on the treatment path.

In some embodiments, the controller is configured to define the treatment path such that a shortest distance between any one of the edge points and the treatment path is at least 0.001 mm.

In some embodiments, the controller is configured to define the treatment path by:
    defining at least one curve passing through the edge points,
    offsetting the curve toward the reference point, and
    defining the treatment path responsively to the offset curve.

In some embodiments, the controller is configured to define the treatment path responsively to the offset curve by defining the treatment path as a perimeter of a predetermined shape inscribed within the offset curve.

In some embodiments, the predetermined shape is an ellipse.

In some embodiments, the controller is configured to define the treatment path responsively to the offset curve by defining the treatment path as a perimeter of a predetermined shape of maximal area inscribed within the offset curve.

In some embodiments, the controller is configured to define the treatment path responsively to the offset curve by defining the treatment path as a perimeter of a predetermined shape of maximal area centered at the reference point and inscribed within the offset curve.

In some embodiments, the controller is configured to define the treatment path responsively to the offset curve by defining the treatment path as a closed curve inscribed within the offset curve and having a shape of a limbus of the eye.

There is further provided, in accordance with some embodiments of the present invention, a method including acquiring an image of an eye, identifying, in the image, multiple edge points at different respective angles relative to a reference point located on the eye radially inward from the edge points, each of the edge points lying on an edge of a respective blood vessel, defining multiple target regions on the eye between the reference point and the edge points, and causing a radiation source to irradiate the target regions.

There is further provided, in accordance with some embodiments of the present invention, a system including a radiation source and a controller. The controller is configured to acquire an image of an eye, to identify, in the image, multiple edge points at different respective angles relative to a reference point located on the eye radially inward from the edge points, each of the edge points lying on an edge of a respective blood vessel, to define at least one curve passing through the edge points, and to offset the curve toward the reference point. The controller is further configured to receive from a user, while displaying the offset curve to the user, a definition of multiple target regions on the eye, and to cause the radiation source to irradiate the target regions.

There is further provided, in accordance with some embodiments of the present invention, a method including acquiring an image of an eye, identifying, in the image, multiple edge points at different respective angles relative to a reference point located on the eye radially inward from the edge points, each of the edge points lying on an edge of a respective blood vessel, defining at least one curve passing through the edge points, and offsetting the curve toward the reference point. The method further includes, while displaying the offset curve to a user, receiving, from the user, a definition of multiple target regions on the eye, and causing a radiation source to irradiate the target regions.

The present invention will be more fully understood from the following detailed description of embodiments thereof, taken together with the drawings, in which:

DETAILED DESCRIPTION OF EMBODIMENTS

Overview

Figure 1:
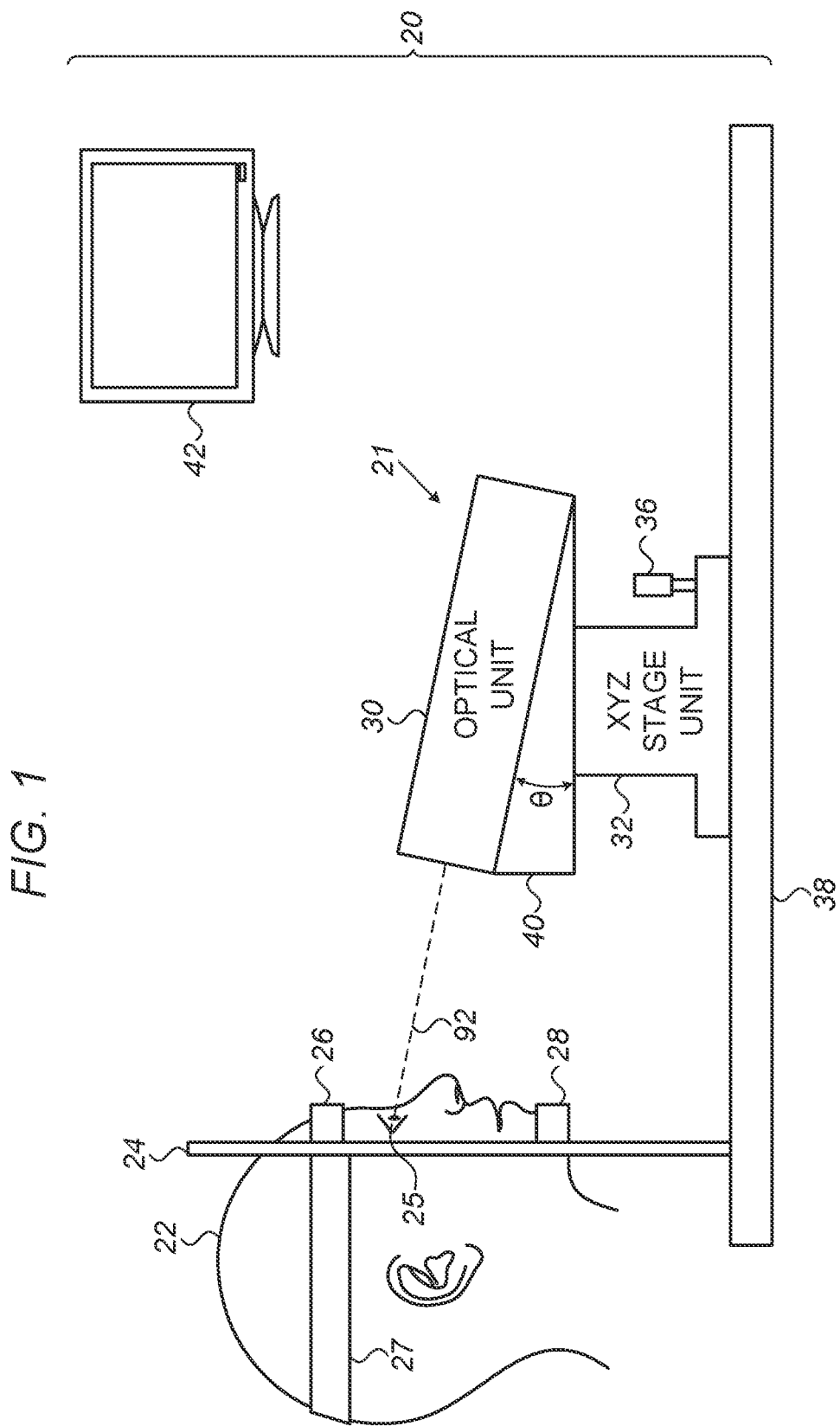
FIG. 1 is a schematic illustration of a system for performing a trabeculoplasty procedure, in accordance with some embodiments of the present invention.

When performing a trabeculoplasty on an eye, it is desirable to avoid irradiating blood vessels, due to the risk of bleeding and/or other adverse effects.

To address this challenge, embodiments of the present invention provide a technique for defining a treatment path that avoids the blood vessels of the eye. Subsequently to defining the treatment path, multiple target regions on the treatment path are defined, and the target regions are then irradiated.

To define the treatment path, a controller first identifies multiple points on the inner edges of blood vessels surrounding the limbus of the eye. Subsequently, the controller defines a curve passing through the points. The controller then offsets the curve inward, toward the center the eye. Finally, the controller inscribes the treatment path within the offset curve.

Notwithstanding the above, in some cases it may not be possible to define the treatment path as described above, e.g., due to an unusual distribution of blood vessels in the eye. Moreover, irradiation of sensitive areas other than blood vessels, such as growths, may also cause adverse effects.

Hypothetically, in view of this challenge, it might be possible to cut out portions of the treatment path that pass through blood vessels and other sensitive areas. However, as the present inventors have observed, it is generally impossible to know, a priori, the degree of sensitivity of an eye to radiation; for example, in some patients, even a direct hit of a laser beam on a blood vessel does not cause bleeding. Thus, avoiding all sensitive areas of the eye may, for some patients, unnecessarily reduce the efficacy of the treatment.

To address this challenge, embodiments of the present invention allow the treatment path to pass through sensitive areas, but continually monitor the eye, using suitable image-processing techniques, as the treatment proceeds. If any problematic change (e.g., bleeding) in the eye is observed, the controller evaluates, for each upcoming target region, the likelihood that irradiation of the upcoming target region will cause a similar change. In response to a high likelihood, the controller may shift or skip the upcoming target region. Thus, advantageously, the treatment path is modified selectively, without unnecessarily compromising the efficacy of the treatment.

For example, in response to observing a change at an irradiated target region, the controller may calculate a risk measure that depends on the type of sensitive anatomical feature at the irradiated target region (if such a feature exists), an estimated amount of radiation energy delivered to this sensitive anatomical feature, the type of sensitive anatomical feature at the upcoming target region (if such a feature exists), and an estimated amount of radiation energy that will be delivered to this sensitive anatomical feature. In response to the risk measure exceeding a predefined threshold, the controller may shift or skip the upcoming target region.

In addition to monitoring the eye for problematic changes, the controller, using suitable image-processing techniques, continually checks for any obstacles lying along the treatment path. In response to detecting an obstacle, one or more target regions may be shifted or skipped.

System Description

Figure 2:
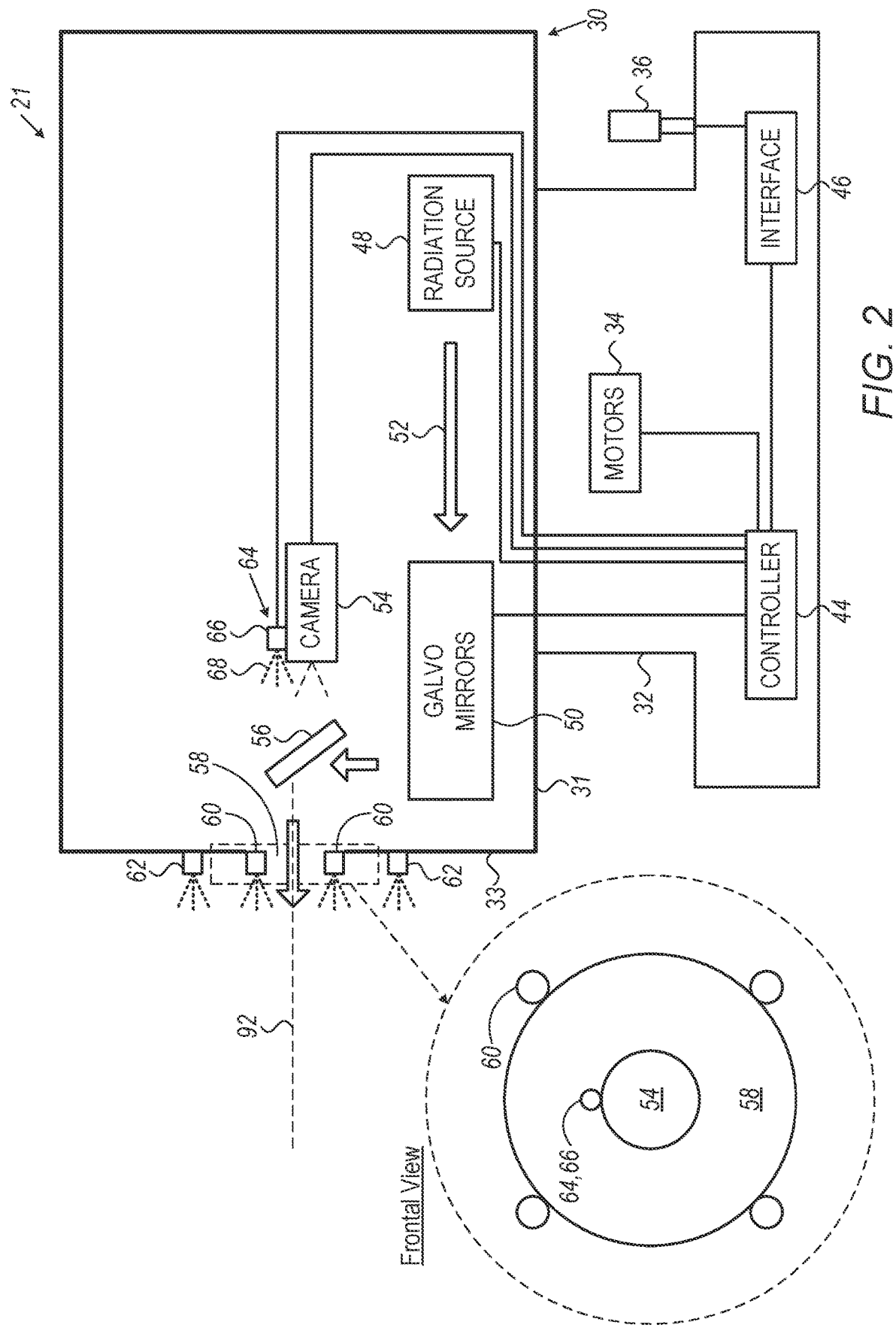
FIG. 2 is a schematic illustration of a trabeculoplasty device, in accordance with some embodiments of the present invention.

Reference is initially made to FIG. 1, which is a schematic illustration of a system 20, comprising a trabeculoplasty device 21, for performing a trabeculoplasty procedure, in accordance with some embodiments of the present invention. Reference is further made to FIG. 2, which is a schematic illustration of trabeculoplasty device 21, in accordance with some embodiments of the present invention.

Trabeculoplasty device 21 comprises an optical unit 30 and a controller 44. Optical unit 30 comprises one or more beam-directing elements, comprising, for example, one or more galvo mirrors 50, which may be referred to collectively as a "galvo scanner," and/or a beam combiner 56. Optical unit 30 further comprises a radiation source 48, which is configured to irradiate an eye 25 of a patient 22 with one or more treatment beams 52 by emitting the treatment beams toward the beam-directing elements such that the beams are directed by the beam-directing elements toward the eye.

More specifically, before the emission of each treatment beam 52 from radiation source 48, or while the beam is being emitted, controller 44 aims the beam-directing elements at the desired target region on eye 25 such that the beam is directed, by the beam-directing elements, toward the target region. For example, the beam may be deflected by galvo mirrors 50 toward beam combiner 56, and then deflected by the beam combiner such that the beam impinges on the target region. (Since each treatment beam impinges on the eye with a non-infinitesimal spot size, the present application generally describes each beam as impinging on a "region" of the eye, rather than impinging at a "point" on the eye.) The beam thus follows a path 92, which extends from the most downstream of the beam-directing elements—such as beam combiner 56—to eye 25.

Typically, the radiation source comprises a laser, such as an Ekspla™ NL204-0.5K-SH laser. The laser may be modified to include an attenuator, an energy meter, and/or a mechanical shutter. Alternatively or additionally to a laser, the radiation source may comprise any other suitable emitter.

In some embodiments, the treatment beams comprise visible light. Alternatively or additionally, the treatment beams may comprise non-visible electromagnetic radiation, such as microwave radiation, infrared radiation, X-ray radiation, gamma radiation, or ultraviolet radiation. Typically, the wavelength of the treatment beams is between 200 and 11000 nm, e.g., 500-850 nm, such as 520-540 nm, e.g., 532 nm. The spatial profile of each treatment beam 52 on the eye may be elliptical (e.g., circular), square, or of any other suitable shape.

Optical unit 30 further comprises a camera 54, which is used by controller 44 to acquire images of the eye. As shown in FIG. 2, camera 54 is typically aligned, at least approximately, with path 92; for example, the angle between path 92 and a hypothetical line extending from eye 25 to the camera may be less than 15 degrees. In some embodiments, the camera is positioned behind beam combiner 56, such that the camera receives light via the beam combiner. In other embodiments, the camera is offset from the beam combiner.

Before the procedure, camera 54 acquires at least one image of eye 25. Based on the image, controller 44 may define the target regions of the eye that are to be irradiated, as further described below with reference to FIGS. 3-4. Alternatively or additionally, based on the image, controller 44 may identify one or more blood vessels or other anatomical features in the eye, as further described below with reference to FIGS. 4-5.

Subsequently, during the procedure, camera 54 may acquire multiple images of the patient's eye at a relatively high frequency. Controller 44 may process these images and, in response thereto, control radiation source 48 and the beam-directing elements so as to irradiate the target regions of the eye while avoiding obstructions and potentially-sensitive anatomical features, as further described below with reference to FIGS. 5-6.

In general, camera 54 may comprise one or more imaging sensors of any suitable type(s), such as a charge-coupled device (CCD) sensor, a complementary metal-oxide-semiconductor (CMOS) sensor, an optical coherence tomography (OCT) sensor, and/or a hyperspectral image sensor. Using the sensors, the camera may acquire two-dimensional or three-dimensional images of any suitable type, such as monochrome images, color images (based, for example, on three color frames), multispectral images, hyperspectral images, optical coherence tomography (OCT) images, or images produced by fusing multiple images of different respective types.

Optical unit 30 further comprises a light source 66, which is aligned, at least approximately, with path 92. For example, the angle between path 92 and a hypothetical line extending from the end of path 92 on eye 25 to light source 66 may be less than 20 degrees, such as less than 10 degrees. Light source 66 is configured to function as a fixation target 64 by transmitting visible fixation light 68, thus helping to stabilize the position of the eye.

In particular, prior to the procedure, patient 22 is instructed to fixate eye 25 on light source 66. Subsequently, during the procedure, by virtue of light source 66 transmitting fixation light 68, eye 25 fixates on the light source, such that the eye's line-of-sight is approximately coincident with path 92 (due to the light source being approximately aligned with the path) and the eye is relatively stable. While the eye fixates on the light source, the radiation source irradiates the eye with treatment beams 52.

In some embodiments, light source 66 comprises a light emitter, such as a light emitting diode (LED). In other embodiments, the light source comprises a reflector configured to reflect light emitted from a light emitter.

Typically, the wavelength of fixation light 68, which may be higher or lower than that of the treatment beams, is between 350 and 850 nm. For example, fixation light 68 may be orange or red, with a wavelength of 600-750 nm, while the treatment beams may be green, with a wavelength of 527-537 nm.

Typically, the optical unit comprises an optical bench, and at least some of the aforementioned optical components belonging to the optical unit, such as the radiation source, the galvo mirrors, and the beam combiner, are coupled to the optical bench. Typically, the optical unit further comprises a front face 33, through which the treatment beams and the fixation light pass. For example, optical unit 30 may comprise an encasement 31, which at least partially encases the optical bench and comprises front face 33. (Encasement 31 may be made of a plastic, a metal, and/or any other suitable material.) Alternatively, front face 33 may be attached to, or may be an integral part of, the optical bench.

In some embodiments, front face 33 is shaped to define an opening 58, through which the treatment beams and the fixation light pass. In other embodiments, the front face comprises an exit window in lieu of opening 58, such that fixation light 68 and treatment beams 52 pass through the exit window. The exit window may be made of a plastic, a glass, or any other suitable material.

Typically, optical unit 30 further comprises one or more illumination sources 60 comprising, for example, one or more LEDs, such as white-light or infrared LEDs. For example, the optical unit may comprise a ring of LEDs surrounding opening 58. In such embodiments, controller 44 may cause illumination sources 60 to intermittently flash light at the eye, as described in International Patent Application Publication WO/2020/008323, whose disclosure is incorporated herein by reference. This flashing may facilitate the imaging performed by the camera, and, by virtue of the brightness of the flashing, may further help constrict the pupil of the eye. (For ease of illustration, the electrical connection between controller 44 and illumination sources 60 is not shown explicitly in FIG. 2.) In some embodiments, illumination sources 60 are coupled to front face 33, as shown in FIG. 2.

To facilitate positioning the optical unit, the optical unit may comprise a plurality of beam emitters 62 (comprising, for example, respective laser diodes), which are configured to shine a plurality of triangulating range-finding beams on the eye, e.g., as described in International Patent Application Publication WO/2020/008323. In some embodiments, beam emitters 62 are coupled to front face 33, as shown in FIG. 2. In other embodiments, beam emitters 62 are coupled directly to the optical bench.

Optical unit 30 is mounted onto an XYZ stage unit 32, which is controlled by a control mechanism 36, such as a joystick. Using control mechanism 36, the user of system 20 may position the optical unit (e.g., by adjusting the distance of the optical unit from the eye) prior to treating the eye. In some embodiments, XYZ stage unit 32 comprises locking elements configured to inhibit motion of the stage unit following the positioning of the stage unit.

In some embodiments, XYZ stage unit 32 comprises one or more motors 34, and control mechanism 36 is connected to interface circuitry 46. As the user manipulates the control mechanism, interface circuitry 46 translates this activity into appropriate electronic signals, and outputs these signals to controller 44. In response to the signals, the controller controls the motors of the XYZ stage unit.

In other embodiments, XYZ stage unit 32 is controlled manually by manipulating the control mechanism. In such embodiments, the XYZ stage unit may comprise a set of gears instead of motors 34.

System 20 further comprises a headrest 24, comprising a forehead rest 26 and a chinrest 28. During the trabeculoplasty procedure, patient 22 presses his forehead against forehead rest 26 while resting his chin on chinrest 28. In some embodiments, headrest 24 further comprises an immobilization strap 27, configured to secure the patient's head from behind and thus keep the patient's head pressed against the headrest.

In some embodiments, as shown in FIG. 1, headrest 24 and XYZ stage unit 32 are both mounted onto a surface 38, such as a tray or tabletop. (In some such embodiments, the headrest is L-shaped, and is attached to the side, rather than the top, of surface 38.) In other embodiments, the XYZ stage unit is mounted onto surface 38, and the headrest is attached to the XYZ stage unit.

Typically, as shown in FIG. 1, while irradiating the patient's eye, the optical unit is directed obliquely upward toward the eye while the eye gazes obliquely downward toward the optical unit, such that path 92 is oblique. For example, the path may be oriented at an angle θ of between five and twenty degrees with respect to the horizontal. Advantageously, this orientation reduces occlusion of the patient's eye by the patient's upper eyelid and associated anatomy.

In some embodiments, as shown in FIG. 1, the oblique orientation of path 92 is achieved by virtue of the optical unit being mounted on a wedge 40, which is mounted on the XYZ stage unit. In other words, the optical unit is mounted onto the XYZ stage unit via wedge 40. (Wedge 40 is omitted from FIG. 2.)

System 20 further comprises a monitor 42, configured to display the images of the eye acquired by the camera. Monitor 42 may be attached to optical unit 30 or disposed at any other suitable location, such as on surface 38 next to device 21. In some embodiments, monitor 42 comprises a touch screen, and the user inputs commands to the system via the touch screen. Alternatively or additionally, system 20 may comprise any other suitable input devices, such as a keyboard or a mouse, which may be used by the user.

In some embodiments, monitor 42 is connected directly to controller 44 over a wired or wireless communication interface. In other embodiments, monitor 42 is connected to controller 44 via an external processor, such as a processor belonging to a standard desktop computer.

In some embodiments, as shown in FIG. 2, controller 44 is disposed within XYZ stage unit 32. In other embodiments, controller 44 is disposed externally to the XYZ stage unit. Alternatively or additionally, the controller may cooperatively perform at least some of the functionality described herein with another, external processor.

In some embodiments, at least some of the functionality of controller 44, as described herein, is implemented in hardware, e.g., using one or more fixed-function or general-purpose integrated circuits, Application-Specific Integrated Circuits (ASICs), and/or Field-Programmable Gate Arrays (FPGAs). Alternatively or additionally, controller 44 may perform at least some of the functionality described herein by executing software and/or firmware code. For example, controller 44 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the controller, produce a machine or special-purpose computer, configured to perform the tasks described herein.

In some embodiments, the controller comprises a system on module (SOM), such as the Varisite™ DART-MX8M.

Defining the Target Regions

Figure 3:
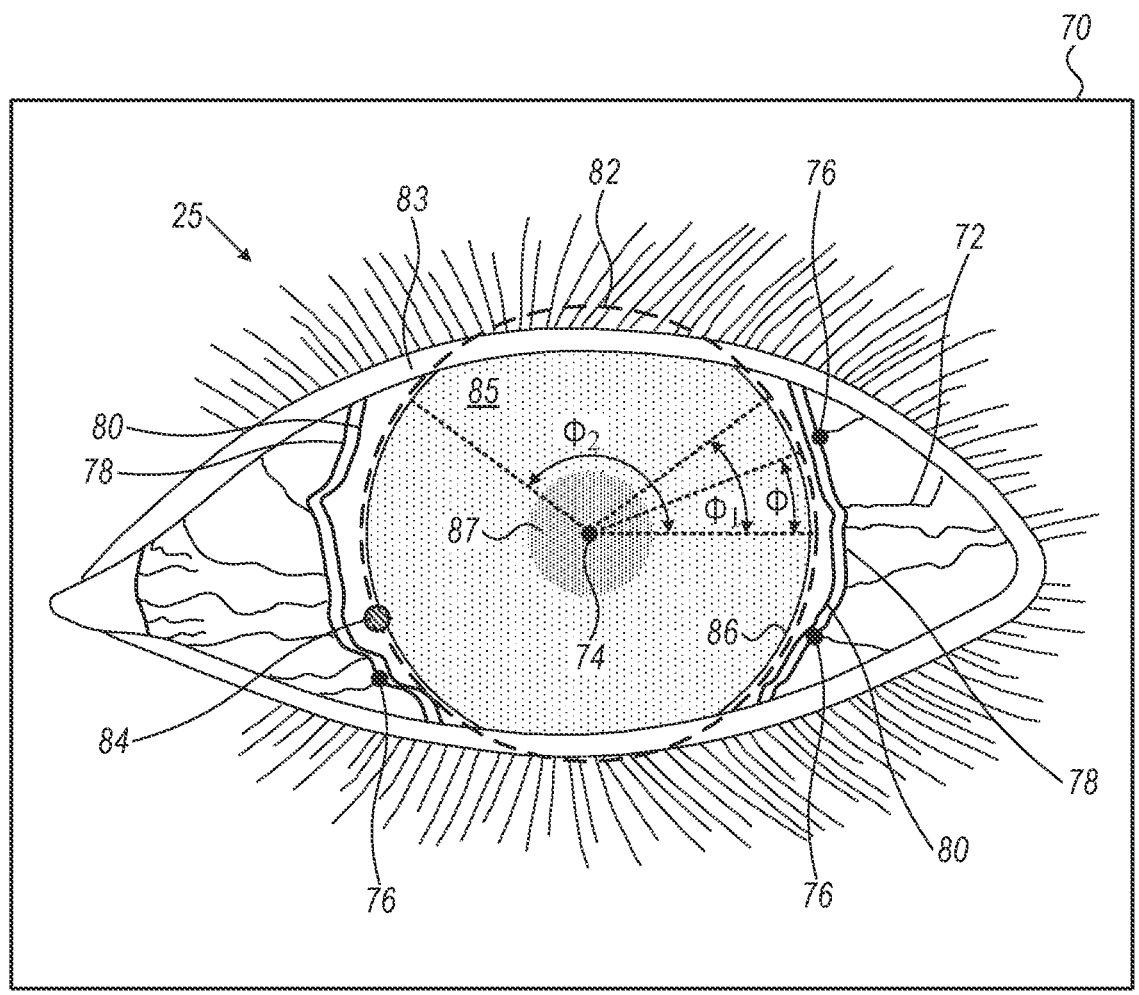
FIG. 3 is a schematic illustration of a technique for defining target regions on an eye, in accordance with some embodiments of the present invention.

Reference is now made to FIG. 3, which is a schematic illustration of a technique for defining target regions 84 on eye 25, in accordance with some embodiments of the present invention.

Typically, as described above with reference to FIGS. 1-2, camera 54 acquires at least one image 70 of eye 25 prior to the treatment of the eye. In some embodiments, based on image 70, controller 44 defines target regions 84 such that the target regions do not lie over any blood vessels 72.

To define the target regions, the controller first identifies, in image 70, multiple edge points 76, each of which lies on an edge of a respective blood vessel 72. Edge points 76 lie at different respective angles φ relative to a reference point 74 located on the eye radially inward from the edge points. Typically, for each angle, the edge on which the edge point lies is closer to reference point 74 than is any other edge of any blood vessel at the angle. (Typically, at least 50 edge points 76 are identified; for simplicity, however, FIG. 3 shows only three edge points 76.)

Subsequently to identifying the edge points, the controller defines target regions 84 between the reference point and the edge points. (Typically, at least 50 target regions are identified; for simplicity, however, FIG. 3 shows only one target region.) For example, the controller may first define at least one treatment path 82 between the edge points and the reference point, and then define the target regions such that each of the target regions lies on treatment path 82 (e.g., such that the center of each of the target regions lies on the treatment path). Successive target regions may be spaced apart from one another by any suitable angle, such as 2-4 degrees. For example, for a 360-degree treatment path, the controller may define between 90 and 180 target regions. (It is noted that, depending on the size of each target region and the spacing angle, successive target regions may overlap with one another.)

In some embodiments, the controller defines a respective edge point and target region for each angle belonging to a predefined set of angles. For those angles at which no blood-vessel edge can be identified, the controller defines a synthetic edge point, which does not actually lie at any blood-vessel edge, at a predefined distance from the reference point.

Typically, the treatment path is defined such that the shortest distance between any one of the edge points and the treatment path is at least 0.1 mm, such as between 0.1 and 1 mm, so as to provide sufficient distance between the target regions and the blood vessels.

In some embodiments, to define the treatment path, the controller first defines at least one curve 78 passing through edge points 76, e.g., using any suitable spline interpolation method known in the art. Subsequently, the controller offsets curve 78 toward the reference point, e.g., by a distance of between 0.001 and 1 mm, so as to define an offset curve 80. Subsequently, the controller defines the treatment path responsively to offset curve 80.

For example, at least a portion of the treatment path may be identical to at least a portion of the offset curve. Alternatively, the treatment path may be defined as the perimeter of a predetermined shape, such as an ellipse (e.g., a circle), inscribed within the offset curve and having any suitable center. For example, the treatment path may be defined as the perimeter of a predetermined shape of maximal area, or a predetermined shape of maximal area centered at reference point 74, inscribed within the offset curve. As yet another alternative, the treatment path may be defined as a closed curve inscribed within the offset curve and having the shape of the limbus 86 of the eye. As yet another alternative, the treatment path may be defined by smoothing offset curve 80 and/or offsetting the offset curve toward the reference point.

In some cases, as shown in FIG. 3, the patient's eyelids obscure the blood vessels within one or more ranges of angles. In such cases, the controller typically defines multiple curves 78 (and hence, multiple offset curves 80), each passing through a different respective exposed range of angles. Subsequently, based on the offset curves, the controller may define a closed treatment path, as described above. Nonetheless, the controller may refrain from defining any target regions within the obscured ranges of angles (along with, optionally, small angular ranges adjacent to the obscured ranges, so as to provide a margin of safety). For example, in the scenario shown in FIG. 3, the controller may refrain from defining any target regions between 41 and $2, given that the patient's upper eyelid 83 obscures blood vessels within this range of angles.

In other cases, the density of edge points within a particular range of angles may be less than a predefined threshold density required by whichever curve-fitting algorithm is used to define curve 78, despite this range of angles being exposed. (The low density may result from inability to identify a sufficient number of blood vessels, e.g., due to the patient being in a vasoconstricted state.) In such cases, the controller may define supplementary points lying on limbus 86 within the range of angles, so as to achieve the threshold density. Subsequently, the controller may define curve 78 such that the curve passes through the edge points and the supplementary points.

Subsequently to defining the target regions, the controller causes radiation source 48 (FIG. 2) to irradiate the target regions. Typically, however, the target regions are irradiated only after the user has approved the target regions. For example, the controller may overlay, on image 70, respective markers indicating the target regions. (Optionally, a marker indicating the treatment path may also be overlaid on the image.) The controller may then allow the user to adjust any of the target regions as required, and then indicate that the target regions are approved. Alternatively or additionally, as described in International Patent Application Publication WO/2020/008323, the controller may simulate the treatment procedure by displaying a live sequence of images of the eye and, while displaying the sequence of images, causing the radiation source to irradiate the target regions with one or more aiming beams, which are visible in the images. In response to viewing the aiming beams in the images, the user may approve the target regions for treatment.

Figure 4:
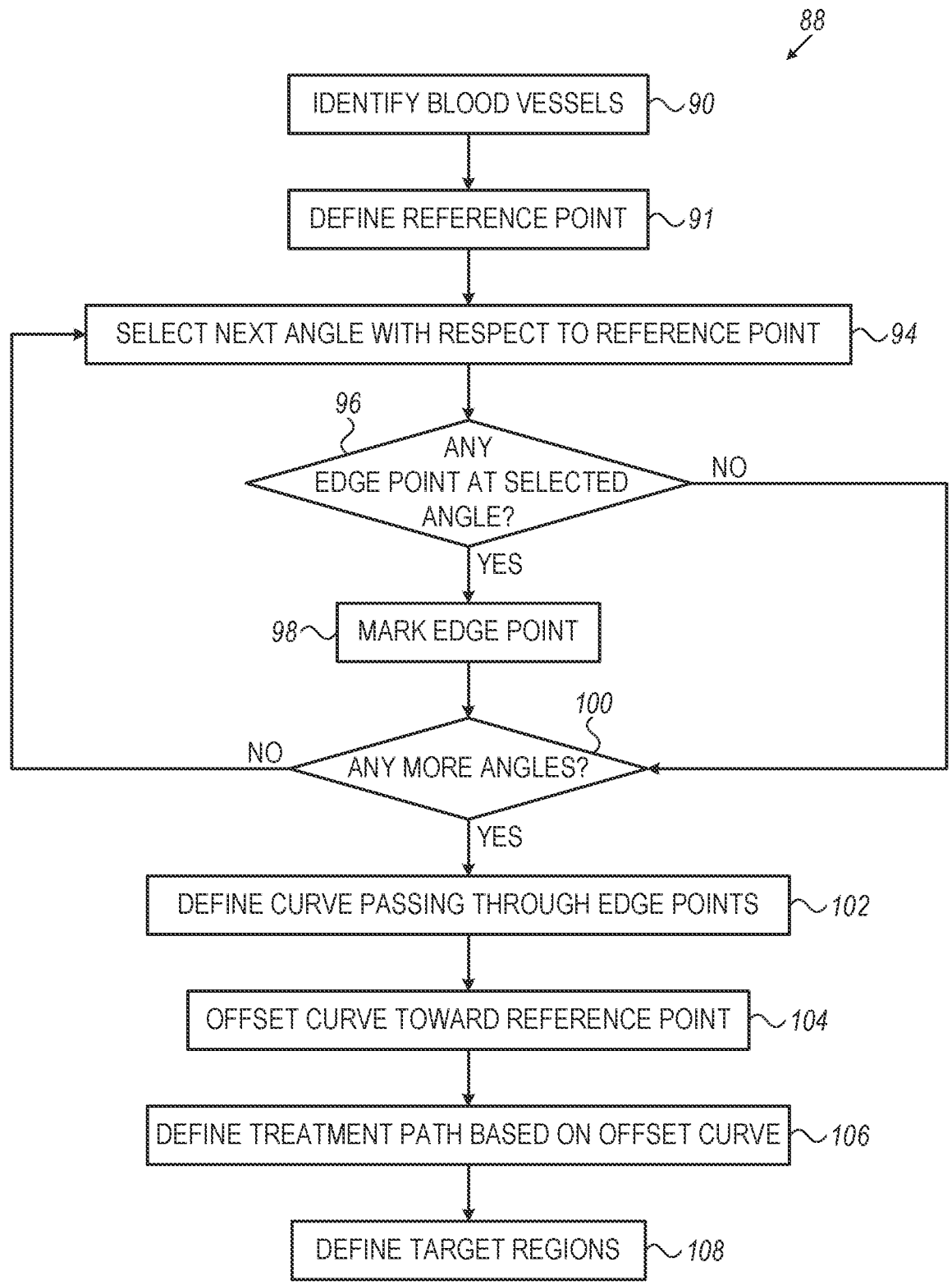
FIG. 4 is a flow diagram for an algorithm for defining target regions, in accordance with some embodiments of the present invention.

For further details regarding the definition of target regions 84, reference is now additionally made to FIG. 4, which is a flow diagram for an algorithm 88 for defining target regions 84, in accordance with some embodiments of the present invention.

Per algorithm 88, the controller first identifies blood vessels in image 70, at a blood-vessel-identifying step 90. To identify the blood vessels, the controller may use segmentation, edge detection, feature enhancement, pattern recognition, and/or any other suitable image-processing techniques. Such techniques are described, for example, in Das, Abhijit, et al., "Sclera recognition-a survey," 2013 2nd IAPR Asian Conference on Pattern Recognition, IEEE, 2013, whose disclosure is incorporated herein by reference.

Subsequently, at a reference-point-defining step 91, the controller defines reference point 14. For example, the controller may identify the iris 85 or pupil 87 of the eye (e.g., using color segmentation), and then place reference point 74 at the center of iris 85 or pupil 87. Alternatively, the controller may identify the limbus of the eye (e.g., using edge detection or maximum gradient detection), and then place the reference point at the center of the limbus. Alternatively, while image 70 is displayed on display 41 (FIG. 1), a user of system 20, using any suitable user interface (e.g., a mouse), may indicate the desired location of the reference point. In response thereto, the controller may place the reference point at the desired location.

Subsequently, the controller iterates through a plurality of angles with respect to the reference point. Each angle is selected at an angle-selecting step 94. Subsequently to selecting the angle, the controller checks, at a first checking step 96, whether there is any edge point at the selected angle. (This check is based on the controller having identified the blood vessels at blood-vessel-identifying step 90.) If yes, the controller marks the edge point, at an edge-point-marking step 98. Subsequently, or if there is no edge point at the selected angle, the controller checks, at a second checking step 100, whether any more non-yet-selected angles remain. If yes, the controller returns to angle-selecting step 94.

In general, the controller may select any suitable angles. For example, the controller may define 0° with respect to any arbitrary axis (such as a horizontal axis, as shown in FIG. 3). Subsequently, during each $i^{th}$ iteration for i=1 . . .

N, the controller may select (i−1)*Δθ, where Δθ may be 0.5°, 1°, or any other suitable value. N, the number of iterations, may be chosen such that 360° lies between (N−1)*Δθ and N*Δθ.

Subsequently to marking the edge points, the controller, at a curve-defining step 102, defines curve 78. The controller then offsets curve 78 toward the reference point, at a curve-offsetting step 104. Subsequently, at a treatment-path-defining step 106, the controller defines the treatment path based on offset curve 80. Finally, the controller defines the target regions, at a target-region-defining step 108. Typically, each target region is specified as an (x, y) offset from reference point 74 or any other suitable reference point; this facilitates compensating for any movement of the eye during the treatment, as described below with reference to FIG. 5.

In alternate embodiments, the controller displays offset curve 80 to the user (by superimposing the offset curve over image 70, over another still image of the eye, or over a live stream of such images), but does not define any target regions. Rather, while the controller displays the offset curve, the controller receives, from the user, the definition of the target regions. For example, the user may define the target regions by clicking a mouse button at each desired target-region location. In response thereto, the controller designates the target regions for irradiation.

Performing the Treatment

Figure 5:
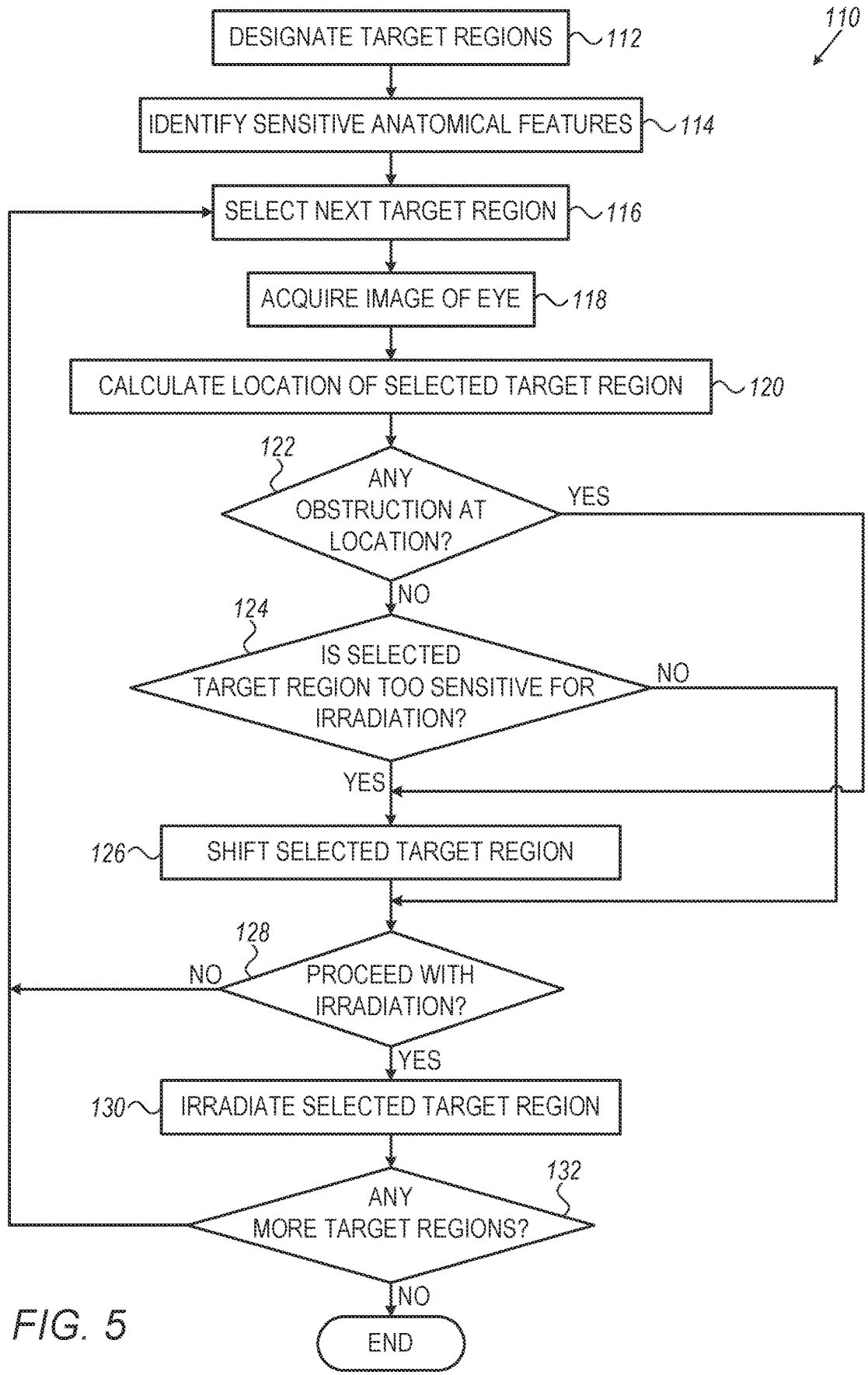
FIG. 5 is a flow diagram for an algorithm for performing an automated trabeculoplasty procedure, in accordance with some embodiments of the present invention.

Reference is now made to FIG. 5, which is a flow diagram for an algorithm 110 for performing an automated trabeculoplasty procedure, in accordance with some embodiments of the present invention.

Algorithm 110 begins with a target-region-designating step 112, at which the controller designates, for irradiation with respective amounts of energy, multiple target regions on the eye of the patient. The respective amounts of energy may be the same; alternatively, one or more amounts of energy may differ from the others.

For example, the controller may define the target regions as described above with reference to FIGS. 3-4. Subsequently, in response to the user's approval of the target regions (as described above with reference to FIG. 3), the controller may designate the target regions for irradiation.

Alternatively, the target regions may be designated using any other technique. For example, as described with reference to FIG. 3 of International Patent Application Publication WO/2020/008323, whose disclosure is incorporated herein by reference, the user may specify the locations of the target regions relative to any suitable reference portion of the eye, such as the limbus. As a specific example, the user may specify an elliptical path of target regions adjacent to the limbus, by specifying the number of target regions and the distance from the limbus at which the center or edge of each of the target regions is to be located. In response to this input, the controller may calculate the location of each of the target regions, and, following approval by the user, designate these regions for irradiation.

In some embodiments, subsequently to designating the target regions, the controller, at an anatomical-feature-identifying step 114, searches at least a portion of the eye for any anatomical features that are likely to possess a heightened sensitivity to radiation. Such anatomical features may include, for example, blood vessels, in the event that the blood vessels were not already identified, e.g., during blood-vessel-identifying step 90 of algorithm 88 (FIG. 4). Alternatively or additionally, such anatomical features may include highly pigmented limbal areas, areas affected by trachoma, a local pemphigoid, a local scleritis, a local burn or another injury, or a growth (e.g., a pterygium, a corneal pannus, an arcus senilis, a dermoid or any other type of limbal tumor, or a limbal pinguecula). Any suitable image-processing techniques, such as those described above with reference to blood-vessel-identifying step 90, may be used to identify the sensitive anatomical features.

In some embodiments, the search for sensitive anatomical features is confined to within a predefined distance (e.g., 1.5, 3, or 5 mm) from treatment path 82 (FIG. 3) or the limbus. In other embodiments, the entire eye is searched.

Next, the controller performs an iterative treatment process. Each iteration begins with a target-region-selecting step 116, at which the controller selects the next one of the target regions that has not yet been irradiated. For example, assuming successive target regions are spaced apart from one another by an angle α, the controller, during each $i^{th}$ iteration for i=1 . . . M, may select the target region located at (i−1)*α. Following the selection of the target region, the controller, using camera 54 (FIG. 1), acquires an image of the eye at an image-acquiring step 118. As described in International Patent Application Publication WO/2020/008323, whose disclosure is incorporated herein by reference, the controller may flash light at the eye while acquiring the image.

Subsequently, based on the image, the controller, at a location-calculating step 120, calculates the location of the selected target region. For example, the controller may first identify the location of a reference point, such as reference point 74 (FIG. 3). Subsequently, the controller may locate the target region by adding the appropriate (x, y) offset to the location of the reference point. Thus, the selected target region may be located even if the eye moved subsequently to target-region-designating step 112.

Next, at a third checking step 122, the controller checks whether there is any static or dynamic obstruction at the location. A static obstruction, whose position relative to the eye is constant, may include, for example, a growth, such as any of the example growths listed above, or a blood vessel on the sclera, limbus, or cornea (e.g., due to corneal neovascularization). A dynamic obstruction, whose position relative to the eye may change during the procedure, may include, for example, an eyelid, eyelashes, a finger, or a speculum.

More generally, in the context of the present application, including the claims, an "obstruction" may be anything other than tissue that is deemed irradiatable by the user of the system. Thus, the scope of the term "obstruction" may vary between procedures. For example, whereas in some procedures a blood vessel may constitute an obstruction, in other procedures irradiation of a blood vessel may be acceptable or even desired, such that a blood vessel is not an obstruction.

In general, obstructions may be identified using any suitable image-processing techniques, optionally in combination with input from the user. For example, prior to the treatment procedure, the user may indicate one or more portions of the eye that constitute potential obstructions, e.g., by identifying these portions in image 70 (FIG. 3). Subsequently, at third checking step 122, the controller may use template matching, edge detection, or any other suitable techniques—including, for example, identifying changes between successive images—to identify the selected portions of the eye. Such techniques may also be used to identify other static or dynamic obstructions that were not necessarily identified in advance by the user.

In the event that an obstruction is identified at the location of the selected target region, the controller refrains from causing the radiation source to irradiate the location. For example, the controller may cause the radiation source to irradiate another location. In other words, the controller may shift the target region, at a target-region-shifting step 126, to avoid the obstruction. (Typically, the target region is shifted away from the pupil, rather than toward the pupil.) Subsequently, the controller may cause the radiation source to irradiate the new location of the target region, at an irradiating step 130.

Alternatively, in the event that an obstruction is identified, the controller may cause the radiation source to irradiate the location of the target region with an amount of energy that is less than the amount of energy that was designated for the target region at target-region-designating step 112. In other words, instead of performing target-region-shifting step 126, the controller may lower the energy in the treatment beams emitted by radiation source 48 (FIG. 2), prior to irradiating the target region at irradiating step 130.

Alternatively, in the event that an obstruction is identified, the current iteration of the treatment process may be terminated without the controller causing the radiation source to irradiate any portion of the eye during the iteration. For example, the controller may return to target-region-selecting step 116 and select the next target region, or terminate the treatment procedure entirely.

If no obstruction is identified at third checking step 122, the controller checks, at a fourth checking step 124, whether the selected target region is too sensitive for irradiation, as described below with reference to FIG. 6. If yes, the controller may shift the target region, lower the energy of the treatment beam, or terminate the iteration (including, optionally, terminating the procedure). Subsequently, or in the event that the selected target region is not too sensitive for irradiation, the controller irradiates the target region at irradiating step 130.

Typically, immediately prior to performing irradiating step 130, the controller performs a fifth checking step 128, at which the controller performs one or more final verifications before proceeding with the irradiation. (Any of these verifications may alternatively be performed at an earlier stage of the iteration.) If, in response to performing the final verifications, the controller decides to proceed with the irradiation, the controller performs irradiating step 130; otherwise, the controller returns to target-region-selecting step 116, image-acquiring step 118, or location-calculating step 120.

For example, as described in International Patent Application Publication WO/2020/008323, the controller may verify that the target region does not lie (even partly) in a predefined "forbidden zone," which is a static region in the field of view of the camera in which, for safety, irradiation is forbidden. Alternatively or additionally, as further described in International Patent Application Publication WO/2020/008323, the controller may verify that the target region is within a predefined distance from a previous target region, indicating that the eye is relatively still. Alternatively or additionally, as further described in International Patent Application Publication WO/2020/008323, the controller may cause the radiation source to fire an aiming beam at the target region, acquire another image of the eye, and then, by processing the latest image, verify that the aiming beam struck the eye within a predefined distance of the target region.

In some embodiments, the controller, at third checking step 122, additionally checks for any obstruction that satisfies one or more predefined criteria, even if the obstruction does not obstruct the selected target region. For example, the controller may check for any obstruction whose size exceeds a predefined threshold or that is moving toward the selected target region. If such an obstruction is identified, the controller may perform target-region-shifting step 126 or any of the alternative functions described above.

Figure 6:
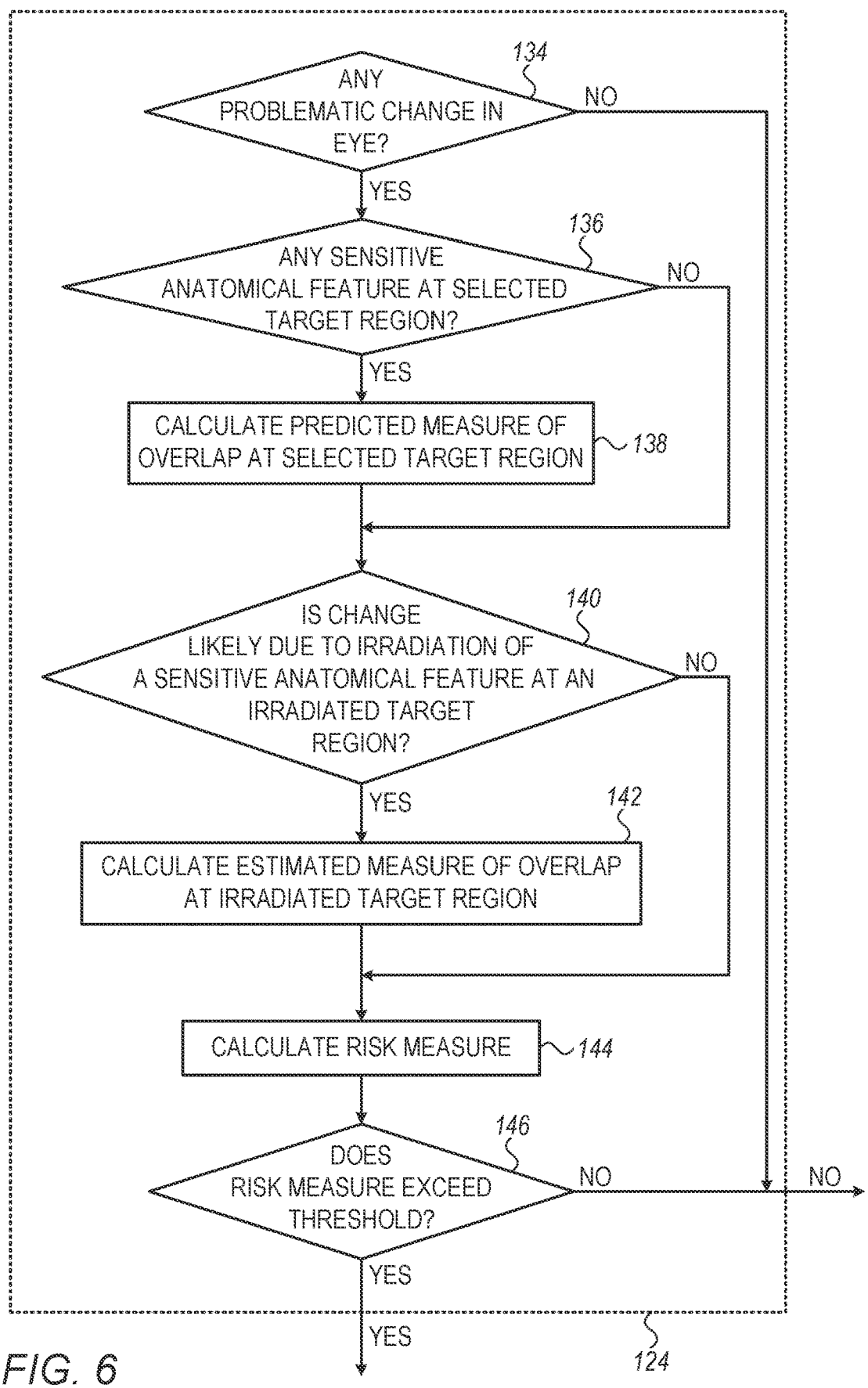
FIG. 6 is a flow diagram for a checking step, in accordance with some embodiments of the present invention.

Reference is now made to FIG. 6, which is a flow diagram for fourth checking step 124, in accordance with some embodiments of the present invention.

Fourth checking step 124 begins with a first assessing step 134, at which the controller processes the latest acquired image, typically together with previously acquired images, so as to ascertain whether a problematic change—such as bleeding, swelling, a change in the density of identifiable blood vessels, and/or a change in color—has occurred in the eye. If no change is identified, the controller decides that the selected target region is not too sensitive for irradiation. Otherwise, the controller may decide that the selected target region is too sensitive for irradiation, as further described below.

In performing first assessing step 134, the controller may use any suitable image-processing techniques, including, for example, optical flow, pattern recognition, edge detection, segmentation, differential checks, and/or color monitoring. For example, the controller may align the latest image with a previously acquired image (such as an image acquired prior to the treatment procedure), using pattern recognition to facilitate the alignment. Subsequently, the controller may subtract the previously acquired image from the current image, and then use edge detection or segmentation to identify the locations of any features of interest—such as a change in color or other features indicating bleeding or swelling—in the difference image.

In response to identifying a problematic change, the controller ascertains, at a second assessing step 136, whether any sensitive anatomical feature (identified at anatomical-feature-identifying step 114 of FIG. 5) is located at the selected target region. In the context of the present application, including the claims, an anatomical feature is said to be located at a target region if any portion of the anatomical feature is within a predefined threshold distance of the target region. The threshold distance is typically defined automatically or semi-automatically, based on (i) the maximum possible movement of the eye between image-acquiring step 118 and irradiating step 130 (FIG. 5), and (ii) the calibration precision of the laser. In some embodiments, the predefined threshold distance is less than 3 mm.

In response to a sensitive anatomical feature being located at the selected target region, the controller, at an overlap-predicting step 138, calculates a predicted measure of overlap between a treatment beam irradiating the selected target region and the anatomical feature. The predicted measure of overlap may be expressed, for example, as an amount of area of the anatomical feature that the beam is predicted to overlap.

In calculating the predicted measure of overlap, the controller may assume that the treatment beam does not deviate from the target region. Alternatively, prior to the procedure, the controller may calculate a probability distribution for the deviation of the treatment beam from the target region, and/or one or more statistics of this distribution such as a maximum, mean, or median deviation. Subsequently, the controller may calculate the predicted measure of overlap based on the statistics, e.g., by assuming that the treatment beam deviates toward the anatomical feature by the maximum, mean, or median deviation.

Subsequently, or if no sensitive anatomical feature is present at the selected target region, the controller ascertains, at a third assessing step 140, whether the change identified at first assessing step 134 is likely due to the irradiation of a sensitive anatomical feature at any one of the irradiated target regions. For example, the controller may check whether any portion of the image showing the change is within a predefined threshold distance of such a sensitive anatomical feature.

If the change is likely due to the irradiation of a sensitive anatomical feature, the controller, at an overlap-estimating step 142, calculates an estimated measure of overlap between the treatment beam that irradiated the target region and the anatomical feature. The estimated measure of overlap may be expressed, for example, as an amount of area of the anatomical feature that the beam is estimated to have overlapped. Subsequently to calculating the estimated measure of overlap, or if the change was likely not due to the irradiation of a sensitive anatomical feature, the controller performs risk-measure-calculating step 144, described below.

Typically, the controller bases the estimate of the measure of overlap on the position of the aiming beam in one or more images acquired close to the time at which the target region was irradiated by the treatment beam. (The firing of the aiming beam at the target region is described above with reference to fifth checking step 128 of FIG. 5.) For example, the controller may assume the treatment beam impinged on (i) the position of the aiming beam in the image acquired immediately before the firing of the treatment beam, or (ii) the position of the aiming beam in the image acquired immediately after the firing of the treatment beam. Alternatively, the controller may compute the average of (i) and (ii), and assume the treatment beam impinged on the eye at this average position.

In addition to estimating and predicting measures of overlap, the controller may calculate an estimated amount of energy delivered (by the treatment beam) to the sensitive anatomical feature at the irradiated target region, along with a predicted amount of energy that will be delivered (by the treatment beam) to the sensitive anatomical feature at the selected target region. Typically, the estimated or predicted amount of delivered energy is a function of the estimated or predicted measure of overlap (respectively), along with parameters that vary with the setup of system 20 (FIG. 1), such as the energy and spot size of the treatment beam.

At risk-measure-calculating step 144, the controller calculates a risk measure associated with irradiating the selected target region. Typically, the risk measure is greater if a sensitive anatomical feature is at the selected target region, relative to if no sensitive anatomical feature is at the selected target region. Moreover, the risk measure is an increasing function of the predicted quantity for the selected target region, given that a higher measure of overlap or amount of delivered energy is more likely to cause another change in the eye. Conversely, typically, the risk measure is greater if the identified change was likely not due to the irradiation of a sensitive anatomical feature, and is a decreasing function of the estimated quantity. Thus, for example, the risk measure may be an increasing function of the ratio of the predicted quantity to the estimated quantity.

Alternatively or additionally, the risk measure may be based on the medical profile of the patient, particularly those aspects of the medical profile related to the sensitivity of the patient's eyes. For example, the risk measure may be based on parameters such as the patient's age, sex, medication history (particularly with regards to use of topical eye medications), frequency of contact lens use, and/or intraocular pressure. Thus, for example, a higher risk measure may be calculated for a patient with a history of topical eye medication use, relative to another patient without such a history.

Alternatively or additionally, the risk measure may be based on the type of anatomical feature at the selected target region. For example, a larger blood vessel may be known, a priori, to have a greater chance of bleeding than a smaller blood vessel; consequently, the risk measure be higher for the former than for the latter.

Alternatively or additionally, the risk measure may be an increasing function of the similarity between the anatomical feature at the selected target region and the irradiated anatomical feature identified at third assessing step 140. The similarity may include, for example, similarity in type, color, and/or size.

Alternatively or additionally, the risk measure may be based on the type of identified change; for example, the risk measure may be higher in response to detecting bleeding or swelling, relative to detecting a mere change in color.

Subsequently to calculating the risk measure, the controller, at a fourth assessing step 146, compares the risk measure to a predefined threshold. If the risk measure exceeds the threshold, the controller decides that the selected target region is too sensitive for irradiation. In response thereto, the controller may refrain from irradiating the target region, or at least lower the energy with which the target region is irradiated, as described above with reference to FIG. 5. Otherwise, the controller decides that the irradiation of the target region may proceed as planned.

In the event that one or more identified changes are likely to have been caused by the irradiation of multiple sensitive anatomical features, the controller considers each of these anatomical features when evaluating the risk for the selected target region. For example, the risk measure may be based on the respective types of the sensitive anatomical features, and/or the respective estimated measures of overlap for the sensitive anatomical features.

It is noted that the flow diagram of FIG. 6 is presented by way of example only, and that many other embodiments of fourth checking step 124 are included within the scope of the present invention. For example:

(i) Alternatively or additionally to ascertaining whether there is a sensitive anatomical feature at the selected target region, the controller may ascertain whether the selected target region is within a predefined threshold distance of a sensitive region of the eye, such as the pupil or an agglomeration of blood vessels. If yes, the risk measure may be increased, optionally as a function of the distance between the target region and the sensitive region.

(ii) In response to identifying a problematic change, the controller may acquire and process additional images, prior to proceeding with the remainder of fourth checking step 124. The processing of the additional images may allow the controller to verify the change, identify the type of change, and/or monitor the change for safety purposes. Thus, for example, the treatment procedure may be terminated if bleeding does not stop within a predefined duration of time or if the area covered by blood exceeds a predefined threshold.

(iii) The controller may decide that the selected target region is too sensitive for irradiation, even without calculating a risk measure. For example, such a decision may be made immediately following an ascertainment of the presence of a sensitive anatomical feature at second assessing step 136. Alternatively, such a decision may be made in response to the predicted measure of overlap, or the predicted amount of delivered energy, exceeding a predefined threshold, which may be an absolute number or a number derived from the corresponding estimate for an irradiated target region identified at third assessing step 140. Alternatively, such a decision may be made in response to the sensitive anatomical feature at the selected target region and the irradiated anatomical feature being of the same type.

Figure 7:
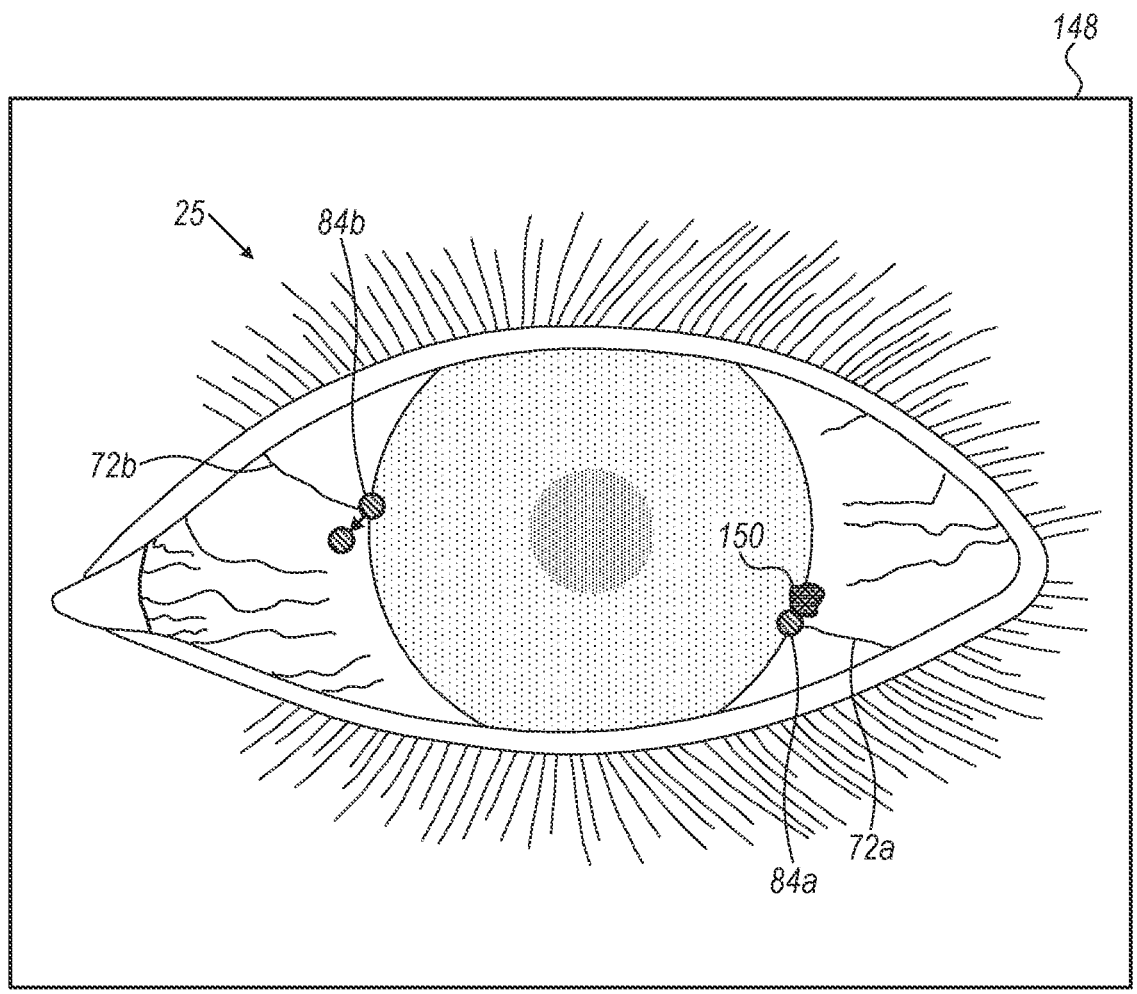
FIG. 7 pictorially illustrates an example performance of a checking step, in accordance with some embodiments of the present invention.

Reference is now made to FIG. 7, which pictorially illustrates an example performance of fourth checking step 124, in accordance with some embodiments of the present invention.

FIG. 7 shows an image 148 of eye 25, which is acquired at image-acquiring step 118 (FIG. 5). By processing image 148 as described above with reference to first assessing step 134 of FIG. 6, the controller may identify a blood pool 150 near an irradiated target region 84a. Blood pool 150 indicates that the irradiation of target region 84a likely caused a first blood vessel 72a, which is located at target region 84a, to bleed. Hence, prior to irradiating another target region 84b, the controller may shift target region 84b away from a second blood vessel 72b, thus reducing the likelihood of another bleeding incident.

Although the above description pertains mainly to trabeculoplasty procedures, it is noted that embodiments of the present invention may be applied to any type of procedure in which target regions of the eye are irradiated, such as a transscleral cyclophotocoagulation (TSCPC) or tissue shrinkage procedure.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a radiation source; and
a controller, configured to:
designate, for irradiation, multiple target regions on an eye of a patient, and
perform an iterative process that includes, during each iteration of the process:
acquiring an image of the eye,
based on the image, calculating a location of a different respective one of the target regions,
processing the image so as to identify any obstruction at the location, and
provided no obstruction at the location is identified, causing the radiation source to irradiate the location.

2. The system according to claim 1, wherein the process further includes, during at least one iteration of the process:
by processing the image, identifying an obstruction at the location, and
in response to identifying the obstruction, refraining from causing the radiation source to irradiate the location.

3. The system according to claim 2, wherein refraining from causing the radiation source to irradiate the location includes causing the radiation source to irradiate another location instead of the location.

4. The system according to claim 2, wherein refraining from causing the radiation source to irradiate the location includes terminating the iteration without causing the radiation source to irradiate any portion of the eye during the iteration.

5. The system according to claim 2, wherein the obstruction includes a blood vessel.

6. The system according to claim 5,
wherein the controller is configured to designate the multiple target regions for irradiation with respective amounts of energy, and
wherein the process further includes, during at least one iteration of the process:
by processing the image, identifying an obstruction at the location, and
in response to identifying the obstruction, causing the radiation source to irradiate the location with another amount of energy that is less than the amount of energy designated for the target region.

7. A method, comprising:
designating, for irradiation, multiple target regions on an eye of a patient; and
performing an iterative process that includes, during each iteration of the process:
acquiring an image of the eye,
based on the image, calculating a location of a different respective one of the target regions,
processing the image so as to identify any obstruction at the location, and
provided no obstruction at the location is identified, causing a radiation source to irradiate the location.

8. The method according to claim 7, wherein the process further includes, during at least one iteration of the process:
by processing the image, identifying an obstruction at the location, and
in response to identifying the obstruction, refraining from causing the radiation source to irradiate the location.

9. The method according to claim 8, wherein refraining from causing the radiation source to irradiate the location includes causing the radiation source to irradiate another location instead of the location.

10. The method according to claim 8, wherein refraining from causing the radiation source to irradiate the location includes terminating the iteration without causing the radiation source to irradiate any portion of the eye during the iteration.

11. The method according to claim 8, wherein the obstruction includes a blood vessel.

12. The method according to claim 11,
wherein designating the multiple target regions for irradiation comprises designating the multiple target regions for irradiation with respective amounts of energy, and
wherein the process further includes, during at least one iteration of the process:
by processing the image, identifying an obstruction at the location, and in response to identifying the obstruction, causing the radiation source to irradiate the location with another amount of energy that is less than the amount of energy designated for the target region.

* * * * *